United States Patent
Baba et al.

(10) Patent No.: US 6,519,314 B1
(45) Date of Patent: Feb. 11, 2003

(54) X-RAY BASED MEASURING DEVICE

(75) Inventors: Rika Baba, Kokubunji (JP); Ken Ueda, Ome (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/720,204

(22) PCT Filed: Jun. 9, 1999

(86) PCT No.: PCT/JP99/03082

§ 371 (c)(1),
(2), (4) Date: Dec. 22, 2000

(87) PCT Pub. No.: WO99/67657

PCT Pub. Date: Dec. 29, 1999

(30) Foreign Application Priority Data

Jun. 24, 1998 (JP) ............................................. 10-177552

(51) Int. Cl.⁷ .............................................. G01N 23/00
(52) U.S. Cl. ..................................... 378/19; 250/370.09
(58) Field of Search ......................... 378/19; 250/370.09

(56) References Cited

FOREIGN PATENT DOCUMENTS

| JP | 61-160078 | 7/1986 |
| JP | 5-111479 | 5/1993 |
| JP | 7-72256 | 3/1995 |
| JP | 8-10252 | 1/1996 |
| JP | 8-299321 | 11/1996 |

*Primary Examiner*—Craig E. Church
(74) *Attorney, Agent, or Firm*—Antonelli, Terry, Stout & Kraus, LLP

(57) ABSTRACT

An X-ray based measuring device of the invention includes: X-ray imaging means (102, 103, 311) which have their detection areas divided into a plurality of detector units (102a to 102d, 201'), detect X-rays transmitted through an inspection object (106), and pick up X-ray images in interested areas (310, 902, 902') of the inspection object; conversion means (211, 212) for converting analog image signals read from the detector units into digital image data under specified conversion conditions for each of the detector units; and re-conversion means (214, 222) for converting the digital image data obtained for each of the detector units under re-conversion conditions corresponding to the specified conversion conditions, wherein analog image signals are A/D converted into digital image data under optimum conversion conditions for each detector unit, and X-ray images in interested areas of the inspection object are sequentially picked up.

35 Claims, 28 Drawing Sheets

X-RAY BASED MEASURING DEVICE

TECHNICAL FIELD

The present invention relates to an X-ray based measuring device, and more particularly to a technique which can be suitably applied to an X-ray measuring device having a planar X-ray detector.

BACKGROUND ART

In a conventional X-ray based measuring device, after an X-ray image transmitted through an inspection object is first converted into an optical image by an X-ray II (X-ray image intensifier), the optical image is converted into an analog image signal. The analog image signal is converted into a digital image signal (image data) by an A/D converter, is then subjected to known image processing such as filtering and contour enhancement by an image processing circuit, and is displayed on an display as an X-ray image. In recent years, there has been a strong demand for rendering the X-ray based measuring device compact, and attempts have been made to render the device compact through the improvement of an X-ray source and its power supply. Meanwhile, in order to pick up an X-ray image of a large area in one imaging, an imaging system including the X-ray II and a television camera has tended to be large in size, and the X-ray II, in particular, has constituted a large hindrance to the miniaturization of the device because of its basic principle. As a means for overcoming this problem, the development of planar X-ray detectors has been undertaken energetically in recent years, and a method has been developed in which an X-ray image is converted into visible light (optical image) by a scintillator such as a CsI, and after the visible light is converted into electrical signals by photo- diodes formed of such as a-Si (amorphous silicon), the electrical signals are sequentially read by a TFT (thin film transistor) or CMOS (complementary) circuit. In a case where a reading circuit is formed by TFTs, the planar X-ray detector makes it possible to make the screen large. On the other hand, in a case where the reading circuit is formed by a CMOS circuit, a planar X-ray detector of a large screen can be constructed by combining a plurality of CMOS X-ray detectors.

DISCLOSURE OF INVENTION

As a result of studying the conventional art, the present inventors found out the following problems. Conventional measuring devices using planar X-ray detectors have suffered from problems in that the dynamic range is narrow and that the imaging speed is slow. FIGS. 25, 26, 27, and 28 are diagrams explaining a schematic configuration of an example of a conventional X-ray based measuring device. In a case where, in chest roentgenography of a subject, an interested area C (901c) including both the heart and the lung filed and indicated by slanting lines is imaged as an interested area, as shown in FIG. 27, with the conventional measuring device using a planar X-ray detector, a minimum value C1 and a maximum value C2 of detector output values in the interested area C are respectively made to correspond to a minimum value (LSB) and a maximum value (MSB) of an A/D converter which can be subjected to analog-to-digital conversion, so as to make maximum use of the capability of the A/D converter. The thick line 209 shown in FIG. 28 shows the relationship between the range (C1–C2) of the value of the detector output (x-axis) and the range (LSB–MSB) permitting the input (y-axis) to the A/D converter. In the case of the conventional measuring device, thus set, however, as shown in FIG. 25, for example, in the measurement of an interested area A (901a) which includes only a portion close to the heart, i.e., a portion (C1–A1) where pixel values are small, values greater than the maximum value A1 are not inputted to the A/D converter. Similarly, as shown in FIG. 26, in the measurement of an interested area B (901b) in the heart field which includes only a portion (B1–C2) where pixel values are large, values smaller than the minimum value B1 are not inputted to the A/D converter. Hence, effective use is not made of the A/D converter. Thus, with the conventional X-ray based measuring device, there has been a problem in that the detectable range (dynamic range) of the detector is not effectively used in the measurement of areas where the interested areas are small.

The object of the present invention is to provide a technique which makes it possible to enlarge the dynamic range of the measuring device using a planar X-ray detector and permits high-speed imaging, and to provide an X-ray based measuring device which makes it possible to make effective use of the dynamic range of the planar X-ray detector and improve the quality of the image measured. A brief description will be given below of outlines of typical configurations in accordance with the present invention.

(1) An X-ray based measuring device in accordance with the present invention is characterized by comprising: X-ray imaging means which have their detection areas divided into a plurality of detector units, detect X-rays transmitted through an inspection object, and pick up an X-ray image in an interested area of the inspection object; conversion means for converting analog image signals read from the detector units into digital image data under specified conversion conditions for each of the detector units; and re-conversion means for converting the digital image data obtained for each of the detector units under re-conversion conditions corresponding to the specified conversion conditions, wherein the analog image signals are A/D converted into the digital image data under optimum conversion conditions for each of the detector units, and X-ray images in the interested area of the inspection object are sequentially picked up.

(2) The X-ray based measuring device in accordance with the present invention is characterized by comprising: X-ray imaging means which have their detection areas divided into a plurality of detector units, detect X-rays transmitted through an inspection object, and pick up an X-ray image in an interested area of the inspection object; conversion means for converting analog image signals read sequentially from the detector units starting with detecting elements of the detector units which are close to a position where two of the detector units contact with each other into digital image data under specified conversion conditions for each of the detector units; and re-conversion means for converting the digital image data obtained for each of the detector units under re-conversion conditions corresponding to the specified conversion conditions, wherein the analog image signals are converted into the digital image data under optimum conversion conditions for each of the detector units, and X-ray conditions for ensuing imaging are set on the basis of the X-ray image of the inspection object detected by each of the detector units, so as to sequentially pick up X-ray images in the interested area.

Further, the X-ray based measuring devices in (1) and (2) above are also characterized in that (a) setting means is further provided for setting the specified conversion conditions for each of the detector units on the basis of the analog image signals in the interested area set in advance, so as to convert the analog image signals read by each of the detector units into the digital image data; (b) the conversion means has an A/D converter, and a range of an input signal to the A/D converter and a range of a signal detected by the detector unit are made to agree with each other; (c) the conversion means has an A/D converter and linear amplification means for linearly amplifying the signal detected by the detector unit and/or nonlinear amplification means for nonlinearly amplifying the same, so as to change an operating condition of the A/D converter by one of first parameters including a gain and an offset of the linear amplification means and second parameters including a gain and nonlinearity of an input output characteristic of the nonlinear amplification means, or by a combination of the first and second parameters; (d), in (c), the nonlinear amplification means is formed by logarithmic amplification means, and the gain and the nonlinearity are set by a logarithmic slope, an intercept voltage, and an offset voltage; (e) a maximum value and a minimum value in the interested area set in advance are determined for each of the detector units, and X-ray conditions in ensuing imaging are determined on the basis of the maximum value and the minimum value; (f) there are further provided rotating means for rotating about the inspection object X-ray irradiating means for irradiating the inspection object with X-rays and the X-ray imaging means, and reconstructing means for reconstructing an X-ray tomographic image or a three-dimensional reconstructed image of the inspection object on the basis of a plurality of X-ray images picked up; (g), in (f), the rotating means is a means for helically rotating and moving the X-ray irradiating means and the imaging means about the inspection object; and (h) means is provided for changing the interested area set in advance, for each direction in which an image of the inspection object is picked up.

(3) The X-ray based measuring device in accordance with the present invention is characterized by comprising: X-ray imaging means which have their detection areas divided into a plurality of detector units, detect X-rays transmitted through an inspection object, and pick up an X-ray image of the inspection object, wherein analog image signals are read sequentially from the detector units starting with detecting elements of the detector units which are close to a position where two of the detector units contact with each other, and X-ray conditions for ensuing imaging are set on the basis of the X-ray image of the inspection object detected by each of the detector units, so as to sequentially pick up X-ray images in the interested area.

In accordance with the configuration (1), in a case where an X-ray image of the inspection subject is picked up by, for instance, a planar X-ray detector which is apparently formed as a single unit by arranging a plurality of X-ray detector units in an adjoining manner or by a planar X-ray detector whose detection area is regarded as being formed by a plurality of X-ray detector units by controlling the reading of analog image signals, the conversion means first converts analog image signals of the pixels in the interested area into digital image data under optimum conversion conditions most suitable for the X-ray image in the interested area detected (imaged) by each of the X-ray detector units. Next, the re-conversion means re-converts a relationship of correspondence between the analog image signals and the digital image data which is different for each of the X-ray detector units and is based on the specified conversion conditions into a relationship of correspondence between the analog image signals and the digital image data which is set in advance for each of the X-ray detector units. Accordingly, it is possible to effectively use the dynamic range of each X-ray detector unit, and even if A/D converters with limited input capabilities are used, the dynamic range can be expanded as the device without lowering the resolution of the images. In addition, the quality of the X-ray images, i.e., the measured images, can be improved. Further, since reading is effected by splitting one image, high-speed reading becomes possible, thereby permitting high-speed imaging.

In accordance with the configuration (2), in a case where an X-ray image of the inspection subject is picked up by, for instance, a planar X-ray detector which is apparently formed as a single unit by arranging a plurality of X-ray detector units in an adjoining manner or by a planar X-ray detector whose detection area is regarded as being formed by a plurality of X-ray detector units by controlling the reading of analog image signals, analog image signals read sequentially from the detector units starting with detecting elements in the interested area which are closest to a position where two of the detector units contact with each other, and the conversion means converts analog image signals of the pixels in the interested area into digital image data under optimum conversion conditions most suitable for the X-ray image in the interested area detected (imaged) by each of the X-ray detector units. Namely, since the analog image signals outside the interested area are not read, high-speed imaging of the X-ray images becomes possible. Next, the re-conversion means re-converts a relationship of correspondence between the analog image signals and the digital image data which is different for each of the X-ray detector units and is based on the specified conversion conditions into a relationship of correspondence between the analog image signals and the digital image data which is set in advance for each of the X-ray detector units. Accordingly, it is possible to effectively use the dynamic range of each X-ray detector unit, and even if A/D converters with limited input capabilities are used, the dynamic range can be expanded as the device without lowering the resolution of the images.

In accordance with the configuration (3), in the case of the planar X-ray detector formed by a plurality of X-ray detector units, the line connecting the positions where two X-ray detector units contact each other is set in the vicinity of the center of the planar X-ray detector. In addition, in a case where an examiner sets an interested area on the X-ray image, the interested area is frequently set in the vicinity of the center of the X-ray image. When analog image signals are read from the planar X-ray detector, the analog image signals are sequentially read from the pixels in the interested area which are closest to the line connecting the positions where the two X-ray detector units contact each other in the vicinity of the center of the planar X-ray detector. Accordingly, since the analog image signals outside the interested area are not read, high-speed imaging becomes possible.

BEST MODE FOR CARRYING OUT THE INVENTION

Figure 1:
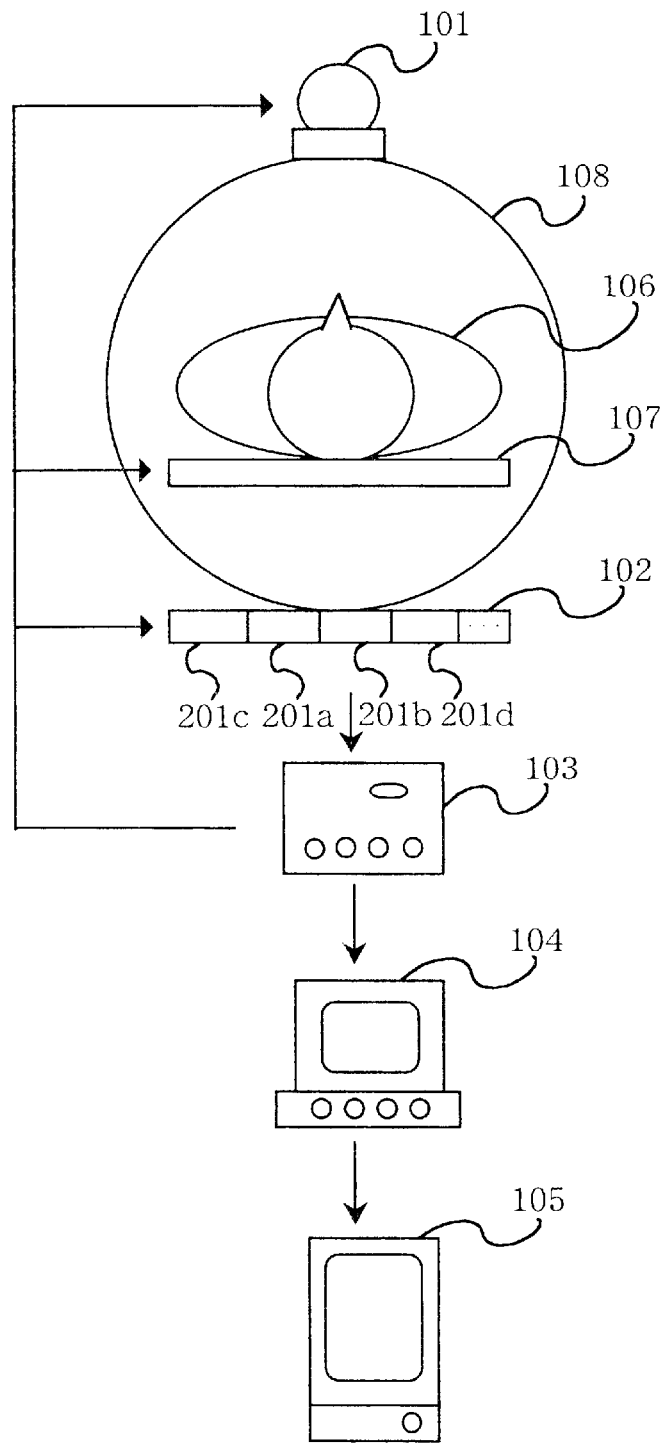
FIG. 1 is a diagram explaining a schematic configuration of an example of a X-ray based measuring device in accordance with a first embodiment of the invention.

Hereafter, referring to the drawings, a detailed description will be given of the mode for carrying out the invention (embodiments). It should be noted that, throughout the drawings explaining the mode for carrying out the invention, those parts or elements having the same functions will be denoted by the same reference numerals, and a repeated explanation thereof will be omitted.

First Embodiment

Description of the Overall Configuration of the Device

FIG. 1 is a diagram explaining a schematic configuration of an example of the X-ray based measuring device in accordance with a first embodiment of the invention. In the X-ray based measuring device (hereafter abbreviated as the "measuring device"), an X-ray generator 101 and a planar X-ray detector 102 (comprised of a plurality of planar X-ray detector units 201a, 201b, 201c, 201d, . . . ) are disposed in an opposing manner with a subject 106 placed therebetween. X-rays radiated from the X-ray generator 101 are applied to the subject 106, and the X-rays transmitted through the subject 106 are detected by the planar X-ray detector 102, thereby picking up an X-ray image concerning the subject 106. From a control room, an examiner (not shown) is capable of changing the position for picking up an X-ray image by, for instance, controlling the position of a moving device 107 for mounting the subject 106 thereon and the position of an imaging system comprised of the X-ray generator 101 and the planar X-ray detector 102, respectively, so as to change the relative positional relationship between the subject 106 and the imaging system. Although, in FIG. 1, the supine position is used as the body position for setting the subject 106 on the moving device 107, the body position may be another position such as an upright position or a lateral position. The configuration of the planar X-ray detector 102 shown in FIG. 1 shows an example of the arrangement of the X-ray detector units such as those shown in FIGS. 9 and 17, but it is possible to adopt an arrangement of the X-ray detector units such as those shown in FIGS. 7, 8, 13, 16, and 23.

The arrows shown in FIG. 1 indicate the flow of data and the flow of control signals. Analog image signals detected by the planar X-ray detector 102 are read by an imaged-data collecting device 103 and are converted into image data of digital signals, are then stored in the imaged-data collecting device 103 and are outputted to a data processor 104. The imaged-data collecting device 103 effects control of the reading of the analog image signals from the planar X-ray detector 102 comprised of a plurality of X-ray detector units, and also effects control of the generation of X-rays from the X-ray generator 101 and control of the positions of the moving device 107 and the planar X-ray detector (control of the position for imaging an image of the subject) on the basis of imaging conditions inputted from a control panel (not shown). It should be noted that a description will be given later of control of the reading of the analog image signals from the planar X-ray detector 102 by the imaged-data collecting device 103. In the data processor 104, the inputted digital image data is subjected to known image processing such as contour enhancement, density correction, and the like, and the digital image data converted into video signals are displayed on an image display 105.

It should be noted that a known cone beam CT device can be constructed by providing a rotating mechanism for rotating the imaging system, which is comprised of the X-ray generator 101 and the planar X-ray detector 102, around the subject 106, by effecting imaging while rotating the imaging system in such a manner as to depict a rotational orbit 108, and by executing computation for reconstructing a tomographic image and/or three-dimensional reconstruction by the data processor 104. Further, a cone beam CT device may be constructed by providing an arrangement in which the imaging system is fixed, and the moving device 107 is provided with a known rotating mechanism to rotate the subject 106. Still further, the imaging system and the moving device 107 may be provided with rotating mechanisms.

<Description of Reading Control>

Figure 2:
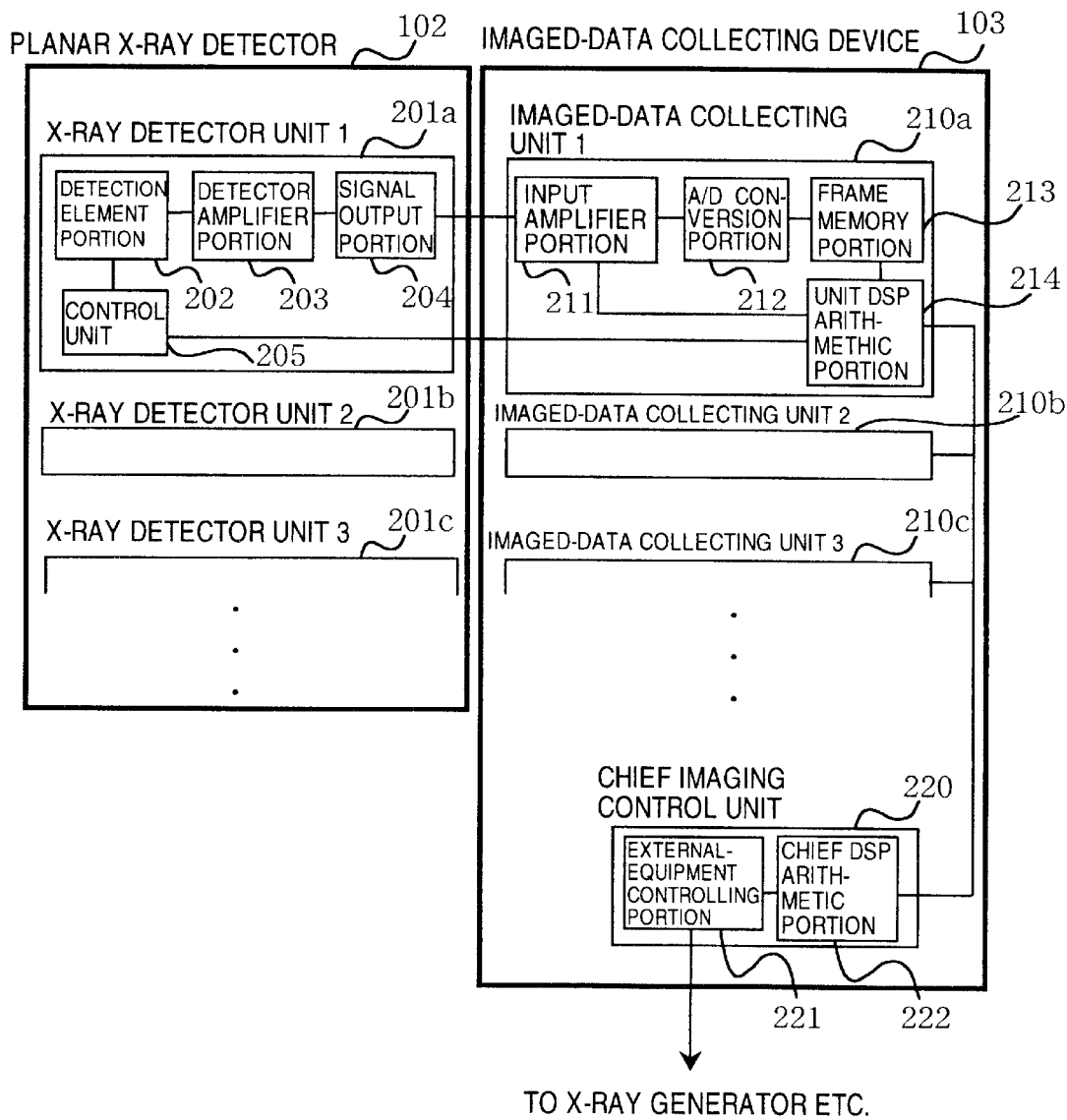
FIG. 2 is a diagram explaining a schematic configuration of examples of a planar X-ray detector and an imaged-data collecting device in accordance with the first embodiment.

FIG. 2 is a diagram explaining a schematic configuration of examples of the planar X-ray detector and the imaged-data collecting device in accordance with the first embodiment. The planar X-ray detector 102 is comprised of an X-ray detector unit 1 (201a), an X-ray detector unit 2 (201b), an X-ray detector unit 3 (201c), . . . , while the imaged-data collecting device 103 is comprised of an imaged-data collecting unit 1 (210a), an imaged-data collecting unit 2 (210b), an imaged-data collecting unit 3 (210c), . . . , and a chief imaging control unit 220. The imaged-data collecting units (210a, 210b, 210c, . . . ) respectively correspond one-to-one with the X-ray detector units (201a, 201b, 201c, . . . ). The imaged-data collecting units (210a, 210b, 210c, . . . ) independently collect analog image signals detected by the X-ray detector units (201a, 201b, 201c, . . . ), respectively. Hereafter, a detailed description will be given of the configurations of the X-ray detector units (201a, 201b, 201c, . . . ) and the imaged-data collecting units (210a, 210b, 210c, . . . ) as well as their operation.

Each X-ray detector unit includes a detection element portion 202 which converts X-rays transmitted through the subject 106 into visible light (optical image) and converts the visible light into electrical signals (analog image signals), a detector amplifier portion 203 for amplifying the analog image signals, a signal outputting portion 204 for sending the amplified analog image signals, and a control portion 205 for controlling the reading (outputting) of the signals from the detection element portion 202. The detection element portion 202 includes a scintillator portion which is composed of CsI or the like and converts an X-ray image into visible light, a plurality of photodiode portions which are composed of amorphous silicon (a-Si), amorphous cesium (a-Se), or the like and convert the visible light into analog image signals, and a switching portion formed by a thin-film transistor for controlling the reading of analog image signals detected by the photodiodes. The control portion 205 of each X-ray detector unit controls the reading of analog image signals from the photodiodes on the basis of a control signal outputted from the imaged-data collecting unit corresponding to each X-ray detector unit. The analog image signals read from the detection element portion 202, after being amplified by the detector amplifier 203, are outputted from the signal outputting portion 204 to an input amplifier portion 211 of the imaged-data collecting unit.

Each imaged-data collecting unit includes the input amplifier portion 211 constituted by a nonlinear amplifier for amplifying the inputted analog image signals and changing the input output characteristics of the signals, an A/D converter portion 212 for converting the amplified analog image signals into digital image signals (image data), a frame memory portion 213 for storing the digital image data, a unit DSP arithmetic portion 214 for performing part of an operation for determining the input output characteristic of the input amplifier portion 211 on the basis of the digital image data stored in the frame memory portion 213, and for controlling the reading of the analog image signals from the X-ray detector unit, and so forth. The chief imaging control unit 220 includes a chief DSP arithmetic portion 222 for controlling the reading (outputting) of signals from the detection element portion 202 of each X-ray detector unit on the basis of the control signal outputted from the imaged-data collecting unit corresponding to each X-ray detector unit, and for performing an operation for determining the input output characteristic of the input amplifier 211 on the basis of the data outputted from the unit DSP arithmetic portion 214 of each imaged-data collecting unit, and an external-equipment controlling portion 221 for controlling the X-ray generator, the moving device, and the like.

As described above, in each X-ray detector unit, the signals outputted from the detection element portion 202 are amplified by the detector amplifier portion 203, and are outputted to the imaged-data collecting unit. The analog image signals inputted to the input amplifier portion 211 are linearly amplified in accordance with the input output characteristic set by the unit DSP arithmetic portion 214, are converted to digital image signals by the A/D converter portion 212, and are sequentially stored in the frame memory of the frame memory portion 213. The unit DSP arithmetic portion 214 performs a predetermined operation by using the signal from the control portion 205 and the digital image data stored in the frame memory portion 213, and outputs the result of operation to the chief imaging control unit 220. The chief DSP arithmetic portion 222 performs a predetermined operation with respect to the inputted result of operation, and outputs the result of operation to the unit DSP arithmetic portion 214. The unit DSP arithmetic portion 214 controls the input output characteristic (amplification factor) of the input amplifier portion 211 on the basis of the result of operation by the chief DSP arithmetic portion 222 so as to change the imaging conditions for the next imaging. Control of the input output characteristic of the input amplifier portion 211 is effected by the imaged-data collecting unit corresponding to each X-ray detector unit and the chief imaging control unit 220 which integrates the imaged-data collecting units.

Figure 3:
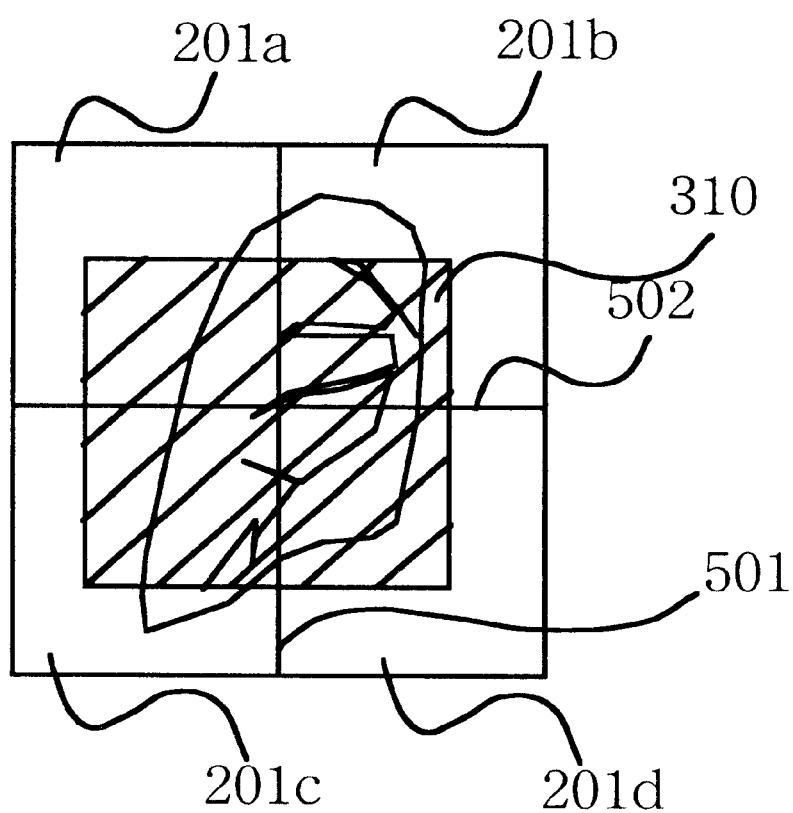
FIG. 3 is a diagram explaining the operation of the imaged-data collecting device in accordance with the first embodiment, and is a diagram explaining an example of the positional relationship between an X-ray detection range in each X-ray detector unit and an interested area.
Figure 4:
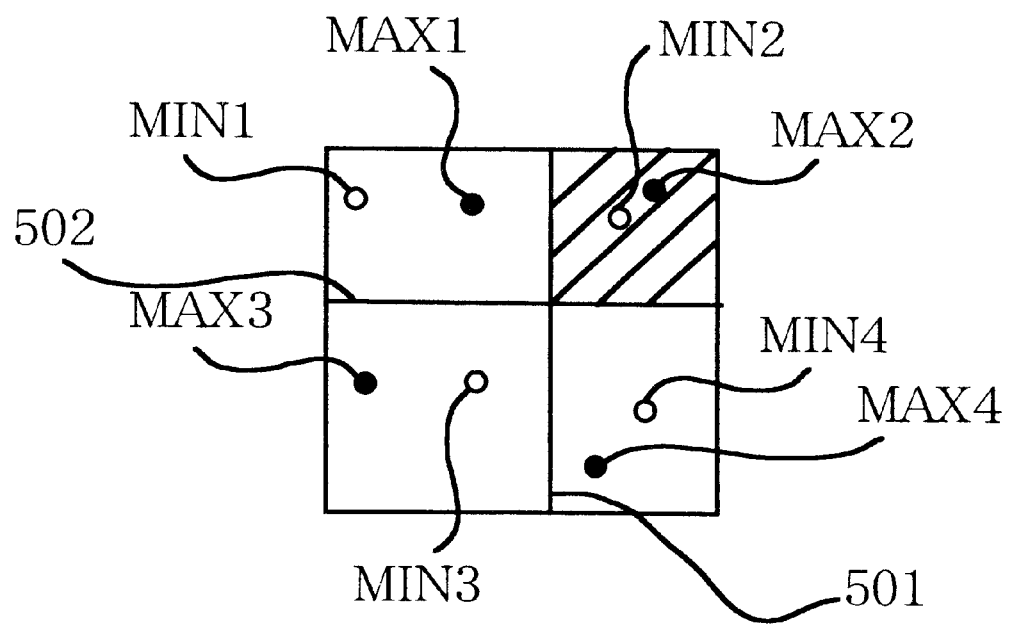
FIG. 4 is a diagram explaining the operation of the imaged-data collecting device in accordance with the first embodiment, and is a diagram illustrating an example of the positions where A/D converted pixels of an X-ray image in an interested area picked up by X-ray detector units assume maximum values and minimum values.
Figure 5:
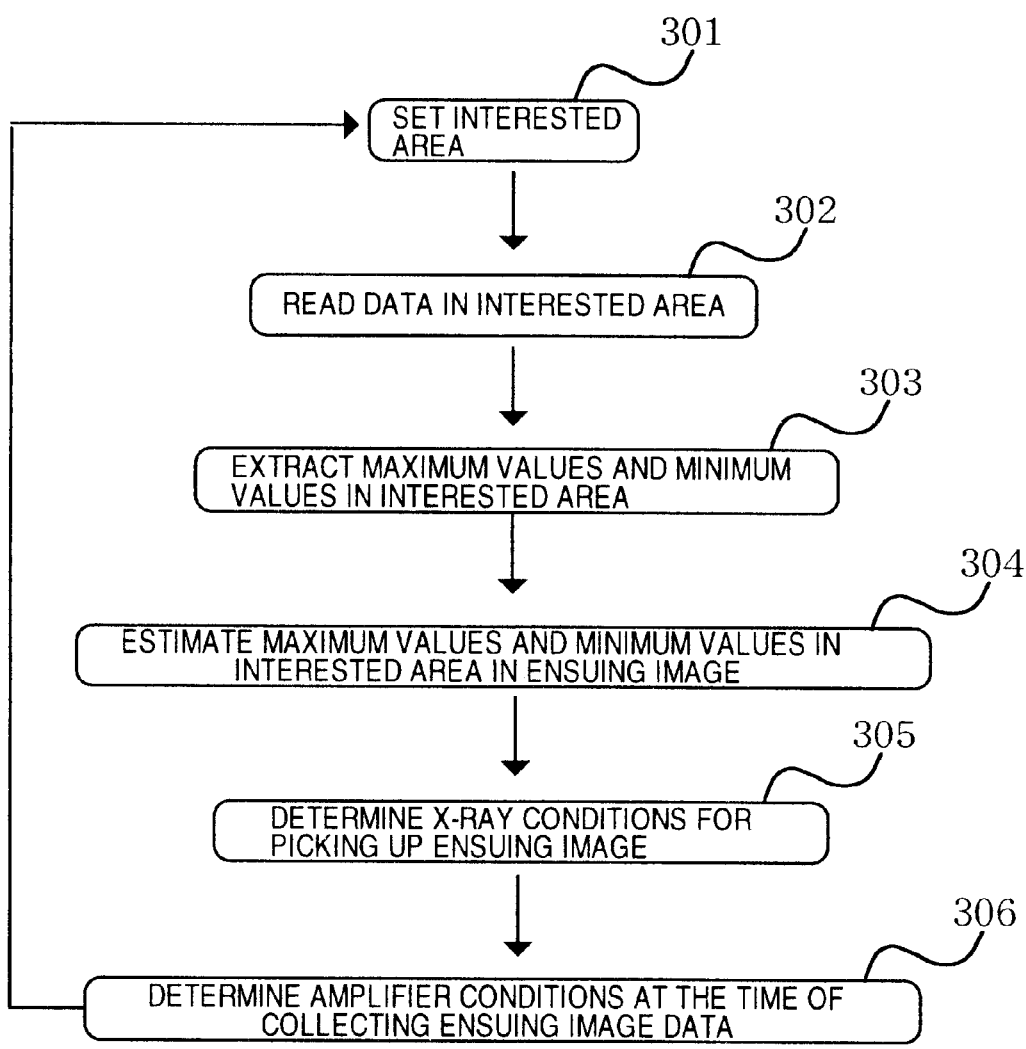
FIG. 5 is a diagram explaining the operation of the imaged-data collecting device in accordance with the first embodiment, and illustrates an example of flow for explaining the operation of the imaged-data collecting device.

Next, referring to FIGS. 3, 4, and 5, a description will be given of the operation of the imaged-data collecting device in accordance with the first embodiment. FIG. 3 is a diagram explaining the operation of the imaged-data collecting device in accordance with the first embodiment, and is a diagram explaining an example of the positional relationship between an X-ray detection range in each X-ray detector unit and an interested area. FIG. 4 is a diagram explaining the operation of the imaged-data collecting device in accordance with the first embodiment, and is a diagram illustrating an example of the positions where A/D converted pixels of an X-ray image in an interested area picked up by X-ray detector units assume maximum values and minimum values. FIG. 5 is a diagram explaining the operation of the imaged-data collecting device in accordance with the first embodiment, and illustrates an example of flow for explaining the operation of the imaged-data collecting device. For the sake of simplification, a description will be given below of an example in which the planar X-ray detector 102 is comprised of the X-ray detector unit 1 (201a), the X-ray detector unit 2 (201b), the X-ray detector unit 3 (201c), and the X-ray detector unit 4 (201d), while the imaged-data collecting device 103 is comprised of the imaged-data collecting unit 1 (210a), the imaged-data collecting unit 2 (210b), the imaged-data collecting unit 3 (210c), and the imaged-data collecting unit 4 (210d). Namely, a description will be given of the case where the numbers of the X-ray detector units and the imaged-data collecting units are four, respectively. The operation of the imaged-data collecting device which will be described below is applicable to a measuring device using the planar X-ray detector 102 constructed by one or more X-ray detector units.

As shown in FIG. 5, when the examiner sets an interested area (Step 301), the chief DSP arithmetic portion 222 outputs to each unit DSP arithmetic portion 214 the range of an interested area 310 for each imaged-data collecting unit to which each unit DSP arithmetic portion 214 belongs. In the example shown in FIGS. 3, 4, and 5, an example is shown in which the examiner gives a designation by fixing the interested area 310 to a specific position in a detector range (imaging range) 311 of the planar X-ray detector 102, but the examiner is also able to give a designation by changing the set position of the interested area 310 for each imaging.

Next, the unit DSP arithmetic portion 214 of each imaged-data collecting unit reads the digital image data from the frame memory portion 213 (Step 302) so as to extract maximum values and minimum values of pixel values in the interested area 310 of the digital image data detected by the X-ray detector units and collected by the corresponding imaged-data collecting units. Namely, as shown in FIG. 4, maximum values MAXi (i=1 to 4) and minimum values MINi (i=1 to 4) in the interested area 310 of the digital image data detected by the X-ray detector units i (i=1 to 4) and collected by the corresponding imaged-data collecting units i (i=1 to 4) are determined. The unit DSP arithmetic portions 214 of the imaged-data collecting units i (i=1 to 4) determine maximum values MAX*i (i=1 to 4) and minimum values MIN*i (i=1 to 4) in which the maximum values MAXi (i=1 to 4) and the minimum values MINi (i=1 to 4) are converted under standard X-ray conditions and amplifier conditions, respectively, and output the same to the chief imaging control unit 220 (Step 303).

Next, the chief DSP arithmetic portion 222 computes, for example, maximum values MAX'=max{MAX*i (i=1 to 4)} and minimum values MINI=min{MIN*i (i=1 to 4)} in the interested area 310 from the maximum values MAX*i (i=1 to 4) and the minimum values MIN*i (i=1 to 4). Further, the chief DSP arithmetic portion 222 estimates maximum values MAXe and minimum values MINe in the interested area 310 in the ensuing imaging of the subject from the maximum values MAX' the minimum values MIN' (Step 304). It should be noted that, as the method of determining the maximum values MAX' the minimum values MIN', maximum values (MAX2) and minimum values (MIN2) of a X-ray detector unit on which attention is particularly focused may be selected apart from the above-described method. Incidentally, the estimation of the maximum values MAXe and the minimum values MINe of pixel values in the interested area 310 in the ensuing imaging is effected, for instance, by extrapolation and interpolation by using polynomial approximation using the maximum values MAX' and the minimum values MIN' obtained from the earlier imaging (since this is a general estimation method, a description thereof will be omitted).

Next, the chief DSP arithmetic portion 222 determines the X-ray conditions in the ensuing imaging on the basis of the estimated maximum values MAXe and minimum values MINe, outputs the X-ray conditions to the unit DSP arithmetic portions 214, and outputs them to the external-equipment controlling portion 221 so as to change the X-ray generating conditions (Step 305). The X-ray conditions in the ensuing imaging are determined such that, for example, the X-ray conditions become proportional to the reciprocal of the square root of the respective estimated minimum value MINe, or the estimated minimum values MINe become fixed. The unit DSP arithmetic portions 214, to which the X-ray conditions have been inputted from the chief DSP arithmetic portion 222, first determine the maximum values and minimum values of the pixel values in the interested area 310 in the ensuing imaging detected by the X-ray detector units i (i=1 to 4) on the basis of the inputted X-ray conditions. Then, the DSP arithmetic portion 214 of each imaged-data collecting unit i (i=1 to 4) determines an amplification factor for causing an input range of the A/D converter 212 and the output range of the input amplifier 211 of each imaged-data collecting unit i (i=1 to 4) to agree with each other from the determined maximum value and minimum value, and the input output characteristics of the input amplifiers 211 are changed on the basis of the amplification factors thus determined (Step 306). Subsequently, an X-ray image is shot, and the image data are fetched again into the frame memory portion 213.

Thus, each imaged-data collecting unit is capable of effecting A/D conversion which makes effective use of the dynamic range of the A/D converter 212 by consecutively performing the processing in Steps 301 to 306 described above. The digital image data for display are sequentially read from the frame memory portion 213 by an image-data reading portion (not shown) before the starting of the next imaging, and after being converted to the standard X-ray conditions and amplifier conditions, the digital image data for display are stored in an image-data storing portion (not shown), are outputted to the data processor 104 where they are subjected to image processing, and are then displayed.

Description of the Method of Setting the Amplifier Input/Output Characteristic

Figure 6:
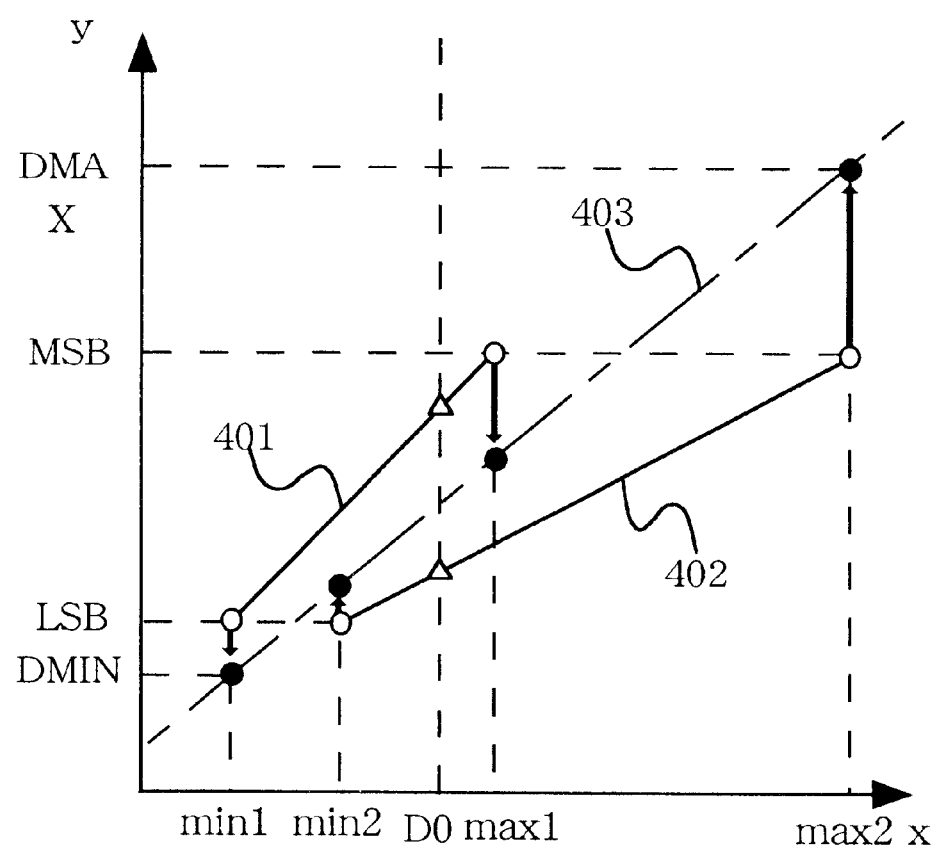
FIG. 6 is a diagram illustrating an example of the input and output characteristics of input amplifier portions for optimizing the reading of analog image signals in the interested area detected by two X-ray detector units in the first embodiment.

FIG. 6 is a diagram illustrating an example of the input and output characteristics of the input amplifier portions for optimizing the reading of analog image signals in the interested area detected by two X-ray detector units in the first embodiment. In FIG. 6, the x-axis shows inputs to the input amplifier portions 211, while the y-axis shows outputs from the input amplifier portions 211. The example shows in FIG. 6 illustrates the relationship between the input values and output values of the amplifiers in a case where maximum values (max1, max2) of the analog image signals in the interested area detected by the X-ray detector unit 1 and the X-ray detector unit 2 are set to maximum values (maximum digital values, MSB) capable of being subjected to analog-to-digital conversion by the A/D conversion portions 212, and minimum values (min1, min2) thereof are set to minimum values (minimum digital values, LSB) capable of being subjected to analog-to-digital conversion by the A/D conversion portions 212. In the input amplifier portions, the inputs (min1 to max1) to the imaged-data collecting unit 1 corresponding to the X-ray detector unit 201a and the inputs (min2 to max2) to the imaged-data collecting unit 2 corresponding to the X-ray detector unit 201b are converted to the same range of output in LSB–MSB. A straight line 401 connecting a point (min1, LSB) and a point (max1, MSB) indicates the input and output characteristic of the input amplifier portion of the imaged-data collecting unit 1, while a straight line 402 connecting a point (min2, LSB) and a point (max2, MSB) indicates the input and output characteristic of the input amplifier portion of the imaged-data collecting unit 1.

As is evident from FIG. 6, in the measuring device in accordance with the first embodiment, even in a case where analog image signals of the same magnitude are inputted to the input amplifier portions of the respective imaged-data collecting units, the input and output characteristic varies for each of the input amplifier portions of the imaged-data collecting units, and the values which are inputted to the A/D conversion portions of the respective imaged-data collecting units differ depending on each imaged-data collecting unit and each imaging. For example, even if the magnitude of the analog image signal is D0, the value after A/D conversion differs as indicated by a Δ (unfilled triangle) mark. In the measuring device in accordance with the first embodiment, the unit DSP arithmetic portion 214 and the chief DSP arithmetic portion 222 convert (re-convert) the digital image data after A/D conversion for each imaged-data collecting unit and imaging into digital image data which are amplified by the input amplifier portion having an amplifier input output characteristic (in the example shown in FIG. 6, when it is assumed that the value of min1 after A/D conversion (converted minimum digital value) is DMIN and the value of max2 after A/D conversion (converted maximum digital value) is DMAX, a function expressing a proportional relationship indicated a chain line connecting the point (min1, DMIN) and a point (max2, DMAX)) for predetermined standard X-ray conditions and amplifier conditions, and which are A/D converted. In the example shown in FIG. 6, the maximum and minimum digital values (MSB, LSB) (indicated by a ○ (unfilled circle) mark) of the A/D converter are converted into converted maximum and minimum digital values (DMAX, DMIN) (indicted by a ● (filled circle) mark). Consequently, the dynamic range of the digital image data can be expanded, i.e., the dynamic range of the measuring device can be easily expanded. Namely, even the A/D conversion portions 212 of a configuration using relatively inexpensive A/D converters having a smaller number of bits are capable of improving the dynamic range of the measuring device. It should be noted that as parameters characterizing the input and output characteristics of the input amplifier portions 211, values of two parameters including an output level when the input is zero, i.e., an offset output, and an increment of the output corresponding to a unit increment of the input, i.e., a gain, are determined, thereby making it possible to set the input and output characteristics 401 and 402 shown in FIG. 6.

Description of Read Scanning by Each X-Ray Detector Unit

Figure 7:
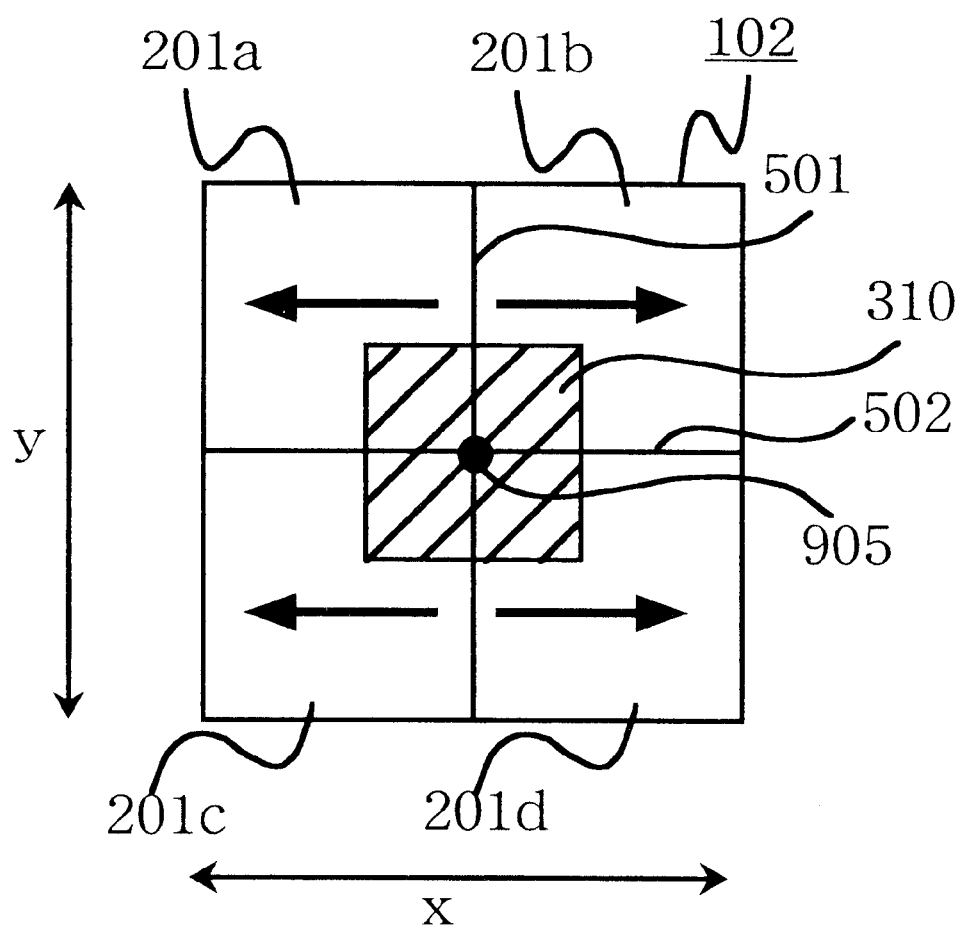
FIGS. 7 and 8 are diagrams explaining the read scanning direction of analog image signals for each X-ray detector unit in the measuring device in accordance with the first embodiment, and illustrate a method of reading analog image signals in the planar X-ray detector 102 constructed by arranging four square X-ray detector units in a square shape.
Figure 8:
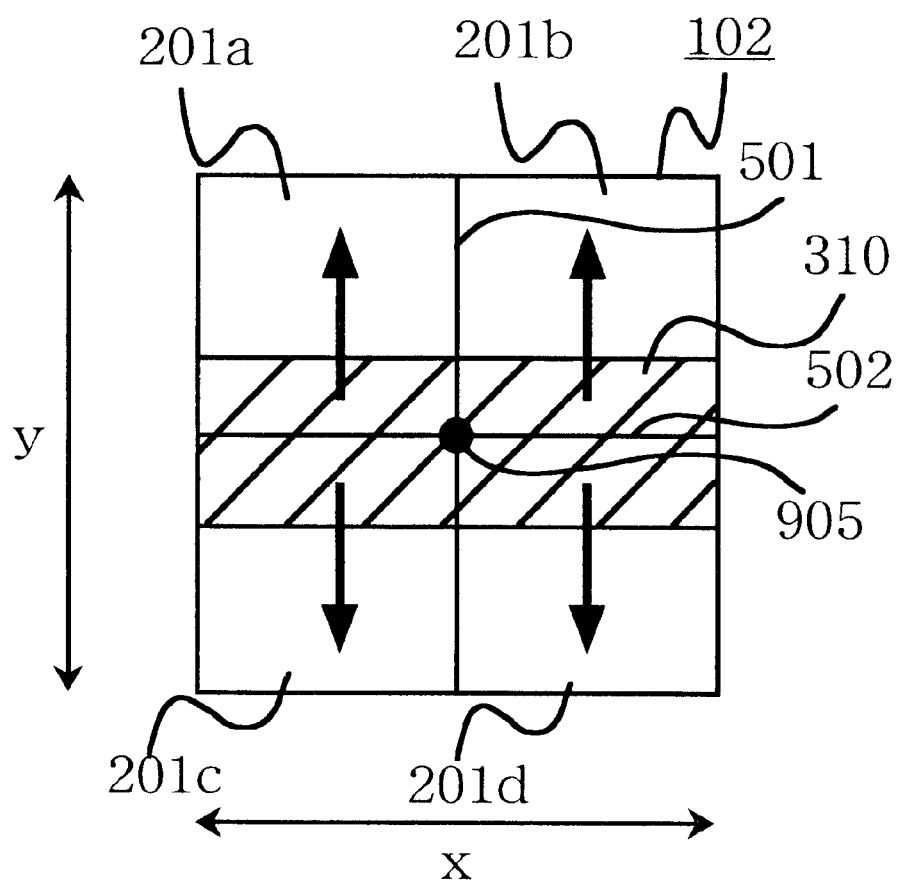
Figure 9:
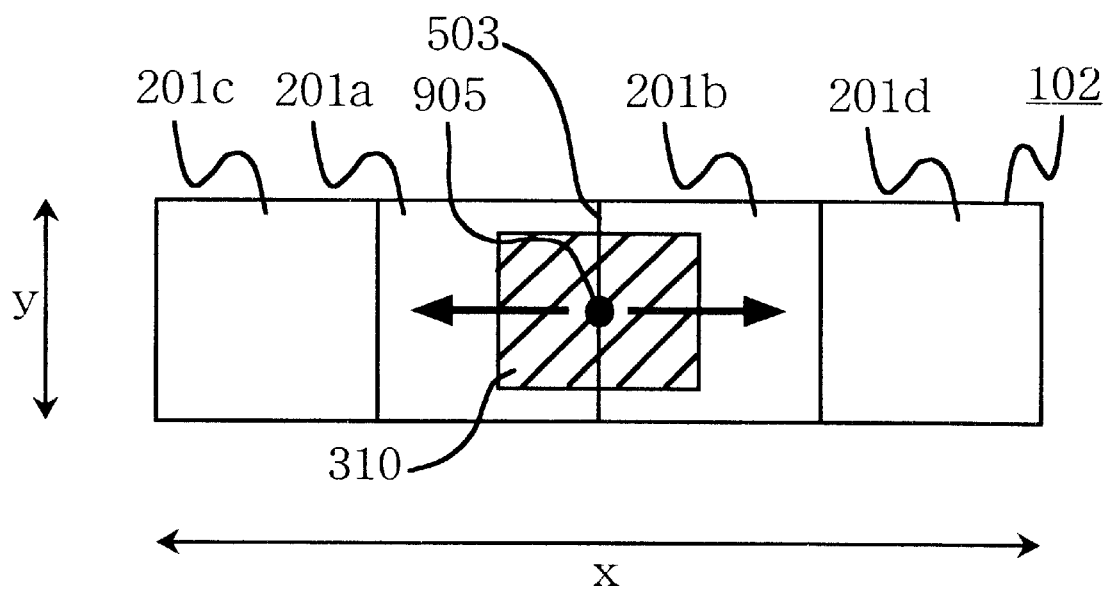
FIG. 9 is a diagram explaining the read scanning direction of analog image signals for each X-ray detector unit in the measuring device in accordance with the first embodiment, and illustrates a method of reading analog image signals in the planar X-ray detector constructed by arranging the four square X-ray detector units in a single row.
Figure 10:
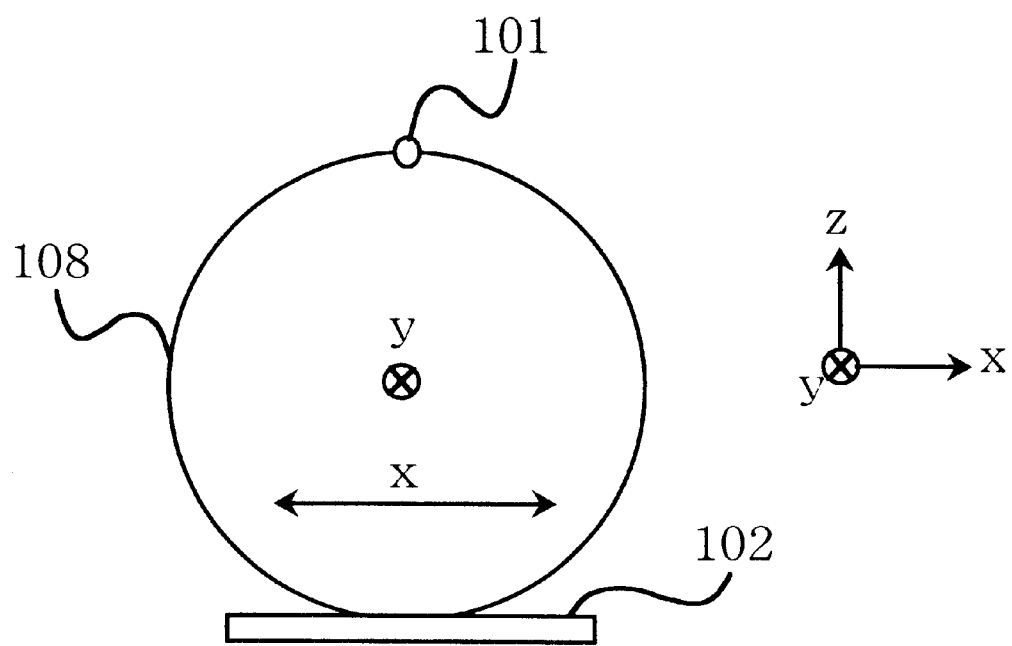
FIG. 10 illustrates the positional relationship between the rotational plane of a imaging system and the planar X-ray detector in the measuring device in accordance with the first embodiment.

FIGS. 7 and 8 are diagrams explaining the read scanning direction of the analog image signals for each X-ray detector unit in the measuring device in accordance with the first embodiment, and illustrate a method of reading analog image signals in the planar X-ray detector 102 constructed by arranging the four square X-ray detector units in a square shape. FIG. 9 is a diagram explaining the read scanning direction of analog image signals for each X-ray detector unit in the measuring device in accordance with the first embodiment, and illustrates a method of reading analog image signals in the planar X-ray detector constructed by arranging the four square X-ray detector units in a single row. FIG. 10 illustrates the positional relationship between the rotational plane of the imaging system and the planar X-ray detector in the measuring device in accordance with the first embodiment. In FIGS. 7, 8, and 9, the area indicated by slanting lines indicates the interested area 310.

A description will be given of the case in which the planar X-ray detector 102 is constructed by arranging the four X-ray detector units 1, 2, 3, and 4 (201a, 201b, 201c, and 201d) in a square shape. As shown in FIG. 7, analog image signals are read in a direction (x direction) parallel to the rotational plane starting with pixels in the interested area at positions closest to a connecting line 501 which represents a position where the X-ray detector unit 1 (201a) and the X-ray detector unit 2 (201b) perpendicular to the rotational plane (x-z plane) of the imaging system formed by the X-ray generator 101 and the planar X-ray detector 102 contact with each other and a position where the X-ray detector unit 3 (201c) and the X-ray detector unit 4 (201d) contact with each other, and which is parallel to a direction (y direction) perpendicular to the rotational plane of the imaging system, and to a connecting line 502 which represents a position where the X-ray detector unit 1 (201a) and the X-ray detector unit 3 (201c) contact with each other and a position where the X-ray detector unit 2 (201b) and the X-ray detector unit 4 (201d) contact with each other, and which is parallel to the rotational plane (x-z plane) of the imaging system. Namely, analog image signals are read simultaneously in the direction of arrows shown in FIG. 7 independently by each of the X-ray detector units 1, 2, 3, and 4 (201a, 201b, 201c, and 201d). Since the analog image signals are simultaneously read independently by the respective X-ray detector units, it is possible to prevent the occurrence of differences in the signal attenuation among the X-ray detector units which is attributable to differences in the time band for reading the analog image signals. Consequently, it is possible to obviate a decline in the accuracy of sensitivity correction in the joints of the X-ray detector units. In the example shown in FIG. 7, the reading of the analog image signals can be effected starting with the pixels in the interested area which are closest to the central position of the visual field, and it is possible to obviate a decline in the image quality in the interested area 310 which is generally set at a position close to the central position of the visual field. Further, the analog image signals in the interested area 310 can be read in an early time band within the reading frame time, and the maximum values and the minimum values in Step 303 shown in FIG. 5 can be acquired in an early time band. Consequently, the computation of the ensuing imaging conditions can be executed in an early time band, so that the time interval in the continuous imaging can be shortened, thereby making it possible to improve the imaging efficiency of the X-ray image.

As shown in FIG. 8, analog image signals are read in a direction (y direction) perpendicular to the rotational plane starting with the pixels in the interested area which are closest to the connecting lines 502 and the connecting line 501. Namely, the analog image signals are read simultaneously in the directions of arrows shown in FIG. 8 independently for the respective X-ray detector units 1, 2, 3, and 4 (201a, 201b, 201c, and 201d). In the same way as in FIG. 7, it is possible to prevent the occurrence of differences in the signal attenuation among the X-ray detector units which is attributable to differences in the time band for reading the analog image signals, and it is possible to obviate a decline in the accuracy of sensitivity correction.

Meanwhile, in the planar X-ray detector 102 of a rectangular shape which is constructed by arranging the four X-ray detector units 1, 2, 3, and 4 (201a, 201b, 201c, and 201d) in a straight line, as shown in FIG. 9, the analog image signals are read starting with the pixels in the interested area which are closest to a connecting line 503 which represents a position where the X-ray detector unit 1 (201a) and the X-ray detector unit 2 (201b) in the central portion of the planar X-ray detector 102 contact with each other and to a central axis passing through centers of y-direction sides of the aforementioned rectangle and parallel to the x direction. Namely, the analog image signals are read simultaneously in the directions of arrows shown in FIG. 9 independently for the respective X-ray detector units 1 and 2 (201a and 201b), and the analog image signals are read starting with the pixels in the interested area which are closest to the central position in the visual field. In the same way as the arrangements shown in FIGS. 7 and 8, it is possible to read the analog image signals in the interested area 310 in an early time band within the reading frame time. Thus, in a case where the width of the planar X-ray detector 102 is enlarged as in the arrangement shown in FIG. 9 to enlarge the width capable of imaging, the maximum values and the minimum values in step 303 shown in FIG. 5 can be acquired in an early time band. Consequently, the computation of the ensuing imaging conditions can be executed in an early time band, thereby making it possible to shorten the time interval in continuous imaging.

In the imaging system shown in FIG. 10, in cases where FIGS. 7, 8, and 9 are applied to a known cone beam CT device in which the imaging system formed by the X-ray generator 101 and the planar X-ray detector 102 is integrated, and the imaging system is rotated around the subject, it is possible to obviate a decline in the accuracy of sensitivity correction in the reading of analog image signals from the planar X-ray detector 102, and to obviate the occurrence of a ring artifact on a reconstructed tomographic image. In particular, in the case where the reading of analog image signals shown in FIG. 8 is applied, reading can be executed starting from the vicinity of a mid-plane in reconstruction, and the interested area which is set at a position close to the mid-plane can be read in an early time band within the reading frame time. Consequently, maximum values and minimum values of the pixel values in the interested area can be acquired in an early time band, and the computation of the ensuing imaging conditions can be executed in an early time band, thereby making it possible to shorten the time interval in continuous imaging. In the case where the reading of analog image signals shown in FIG. 9 is applied, a horizontally elongated visual field can be formed by arranging the X-ray detector units in a direction (x direction) parallel to the rotational plane, so that the visual field of a reconstructed image (CT image) can be enlarged. It should be noted that, in FIG. 10, the circle within the x-z plane indicates the rotational orbit 108 having the y-axis of the imaging system as the center (the subject 106 is not shown).

Description of the Configuration of the Planar X-ray Detector

Figure 11:
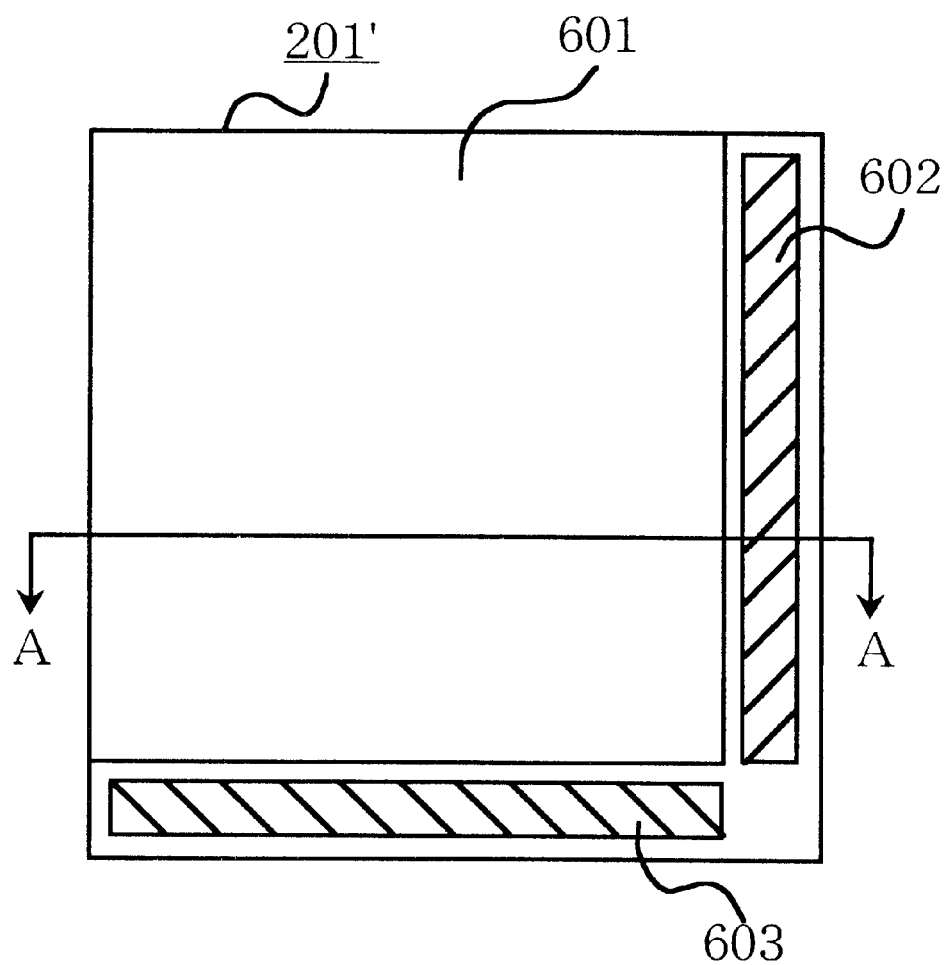
FIG. 11 is a plan view illustrating an example of the X-ray detector unit in accordance with the first embodiment.
Figure 12:
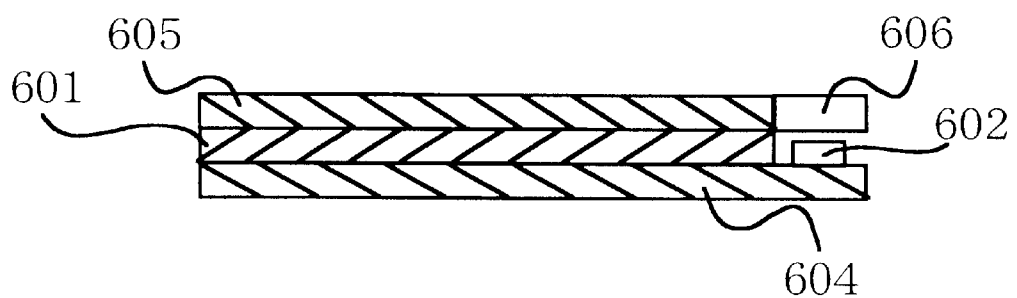
FIG. 12 is a cross-sectional view taken along line A—A shown in FIG. 11.
Figure 13:
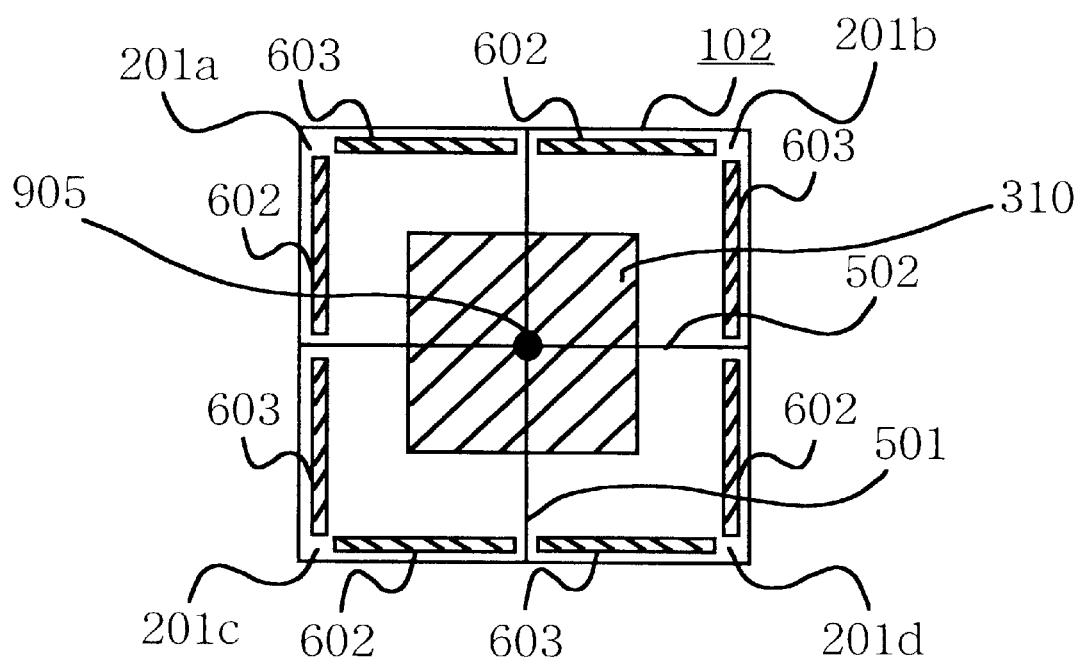
FIG. 13 is a plan view of a planar X-ray detector constructed by using the X-ray detector units shown in FIG. 11.

FIG. 11 is a plan view illustrating an example of the X-ray detector unit in accordance with the first embodiment, FIG. 12 is a cross-sectional view taken along line A—A shown in FIG. 11, and FIG. 13 is a plan view of a planar X-ray detector constructed by using the X-ray detector units shown in FIG. 11. As shown in FIG. 11, an X-ray detector unit 201' is comprised of a light-receiving element array 601 in which a plurality of light-receiving elements are arrayed in the X- and Y-axis directions; a control reading circuit 603 for reading the light accumulated in the light-receiving element array, and a control circuit 602 for controlling the operation of the light-receiving elements. As shown in FIG. 12, in the X-ray detector unit 201', the light-receiving element array 601 and the control circuit 602 for controlling the operation of the light-receiving element array 601 are disposed on an upper surface of a substrate 604. A known scintillator 605 for converting an X-ray image into an optical image is disposed on top of the light-receiving element array. An X-ray shield 606 for preventing X-rays from being directly radiated to the control circuit 602 is disposed on top of the control circuit 602. The X-ray shield 606 is also disposed on top of a region where the control reading circuit 603 is disposed.

In the case where the planar X-ray detector 102 is constructed by arranging the plurality X-ray detector units 201', an arrangement is provided such that, as shown in FIG. 13, the control circuits 602 and the control reading circuits 603 are arranged, and the X-ray shields 606 are disposed on top of these circuit portions, so that nonsensitive regions for preventing the detection of X-rays are arranged on end portions of the four sides. As a result, since the center of the interested area 310 is generally set in a central portion 905 of the planar X-ray detector 102, the missing or the like of image information due to nonsensitive regions does not occur in imaging. In the arrangement shown in FIG. 13, the size of the planar X-ray detector 102 is limited by the sizes of the X-ray detector units 201' used. It should be noted that, in the measuring device of the first embodiment, with respect to the slight missing of image information consequent upon the breakage of light-receiving elements, a defect in the scintillator, or the like, it is possible to avoid an influence on an X-ray image which is displayed, by using pixel values of a plurality of pixels located in the neighborhood of the pixel where the image information is missing and by performing processing such as the estimation of the pixel where the image information is missing by interpolation or substitution.

Figure 14:
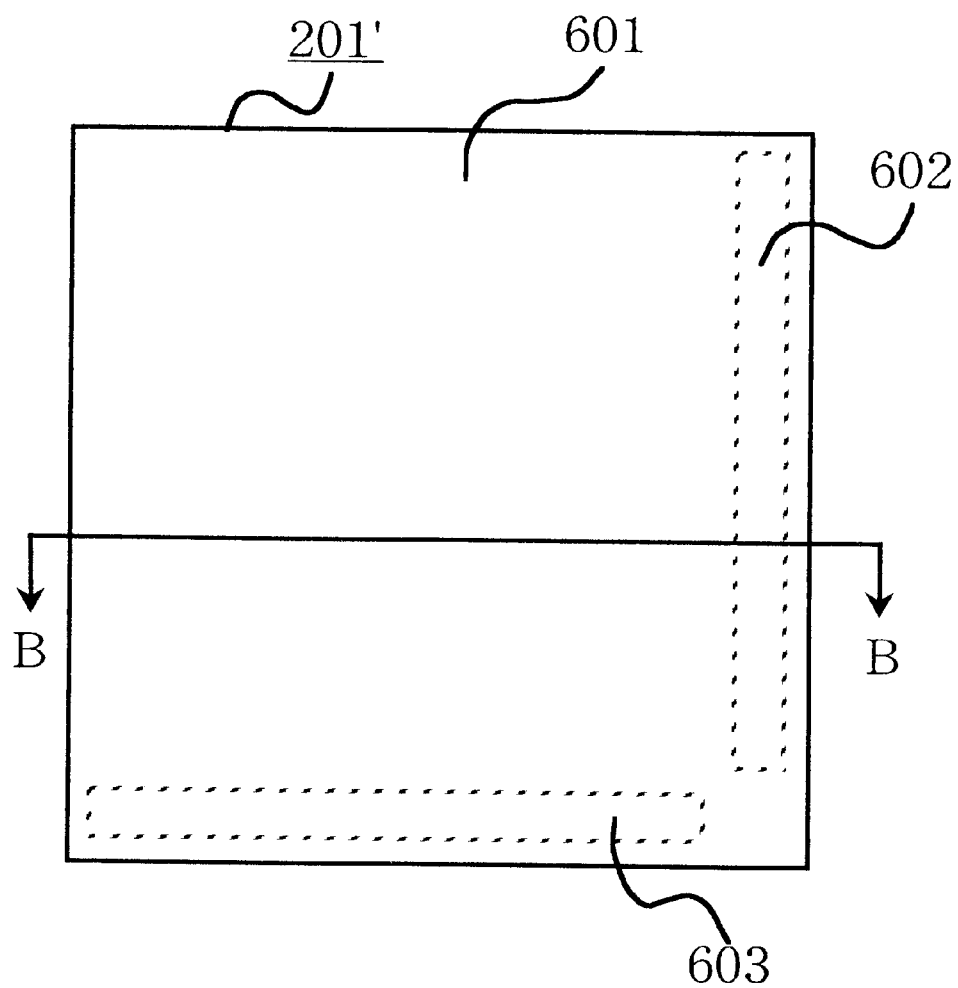
FIG. 14 is a plan view of another example of the arrangement of the X-ray detector unit.
Figure 15:
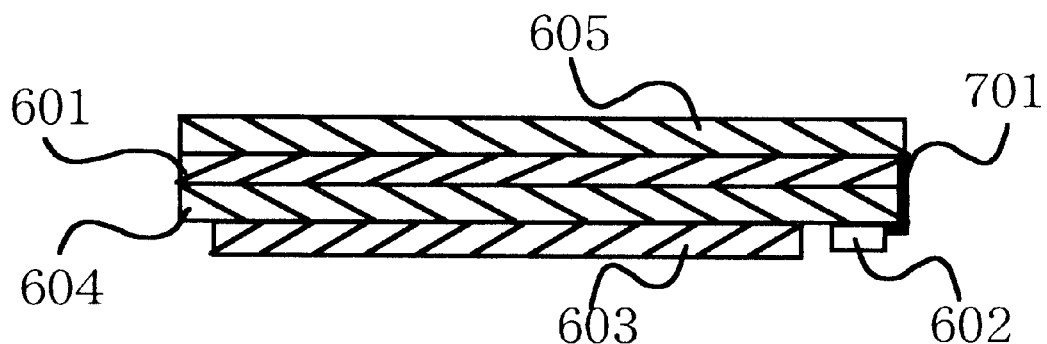
FIG. 15 is a cross-sectional view taken along line B—B in FIG. 14.
Figure 16:
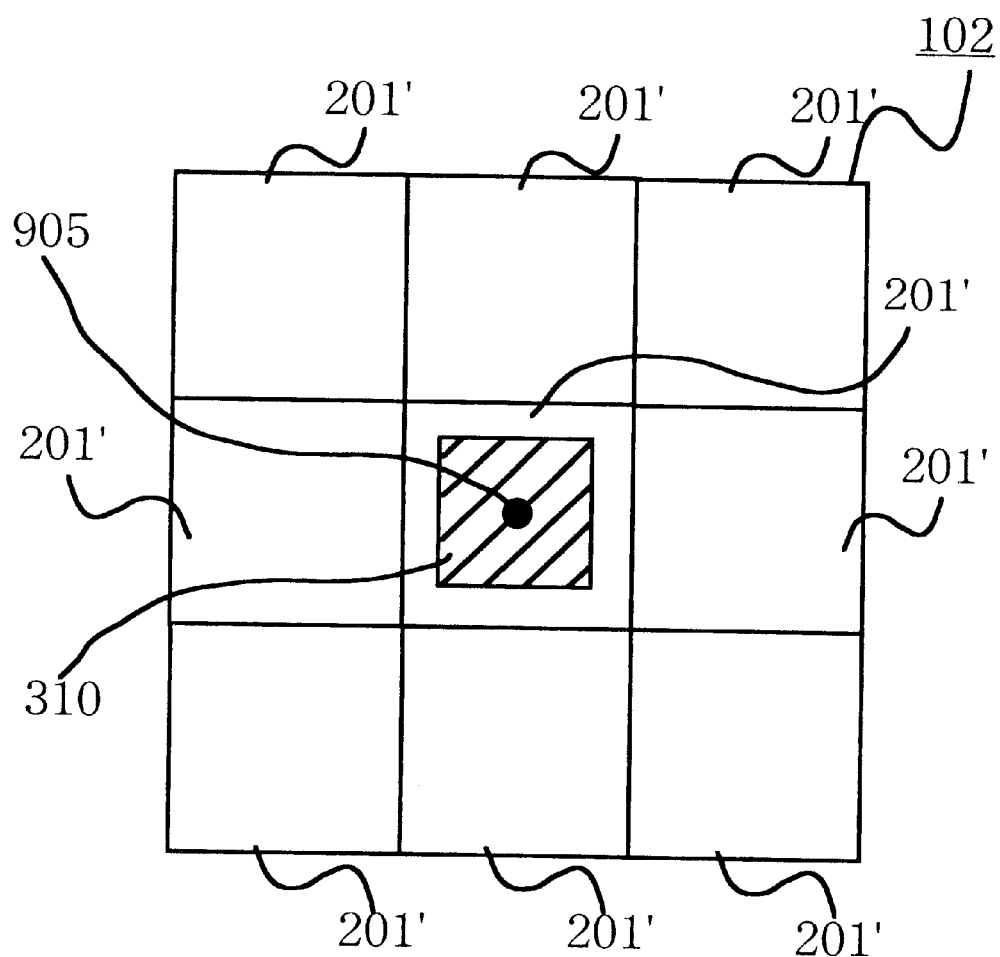
FIGS. 16 and 17 are plan views of the planar X-ray detectors which are constructed by using the X-ray detector units shown in FIG. 14.
Figure 17:
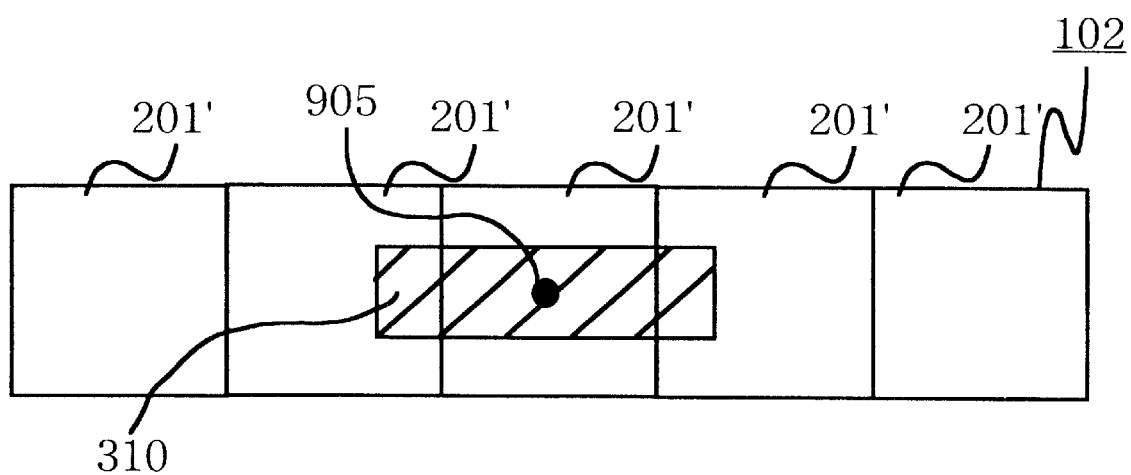

FIG. 14 is a plan view of another example of the arrangement of the X-ray detector unit, FIG. 15 is a cross-sectional view taken along line B—B in FIG. 14, and FIGS. 16 and 17 are plan views of the planar X-ray detectors which are constructed by using the X-ray detector units shown in FIG. 14. As shown in FIG. 15, the light-receiving element array 601 is formed on the upper surface of the substrate 604, and the scintillator 605 is disposed on top of the light-receiving element array 601. The control circuit 602 is disposed in the vicinity of a side of the substrate 604 on the underside of the substrate 604, a signal line (wiring) is disposed on a side surface of the substrate 604, and the control circuit 602 and the light-receiving element array 601 are connected. In the same way as the control circuit 602, the control reading circuit 603 is also disposed in the vicinity of another side of the substrate 604 on the underside of the substrate 604. It should be noted that the signal line (wiring) 701 is disposed so as not to bulge out to the external space of the scintillator 605. As a result, as shown in FIG. 14, the light-receiving element array 601 can be formed on the entire surface of the X-ray detector unit 201', so that the portion of a nonsensitive region where X-rays cannot be detected can be eliminated. As shown in FIGS. 16 and 17, the planar X-ray detector can be constructed by arranging four or more X-ray detector units in an adjoining manner. In this case as well, the center of the interested area 310 is normally located in the central portion 905 of the planar X-ray detector, and analog image signals are sequentially read starting with the detecting elements of the planar X-ray detector which are close to the center of the interested area 310. In the example shown in FIG. 16, the X-ray detector units 201' are arranged squarely to make it possible to enlarge the visual field of the planar X-ray detector, while, as shown in FIG. 17, the effect of scattering rays can be made difficult to be received by arranging the X-ray detector units 201' in a row, thereby making it possible to prevent the deterioration of the quality of the X-ray image. It should be noted that, in FIGS. 16 and 17, the angle of visibility of the planar X-ray detector 102 can be enlarged by using a greater number of X-ray detector units 201'.

Figure 18:
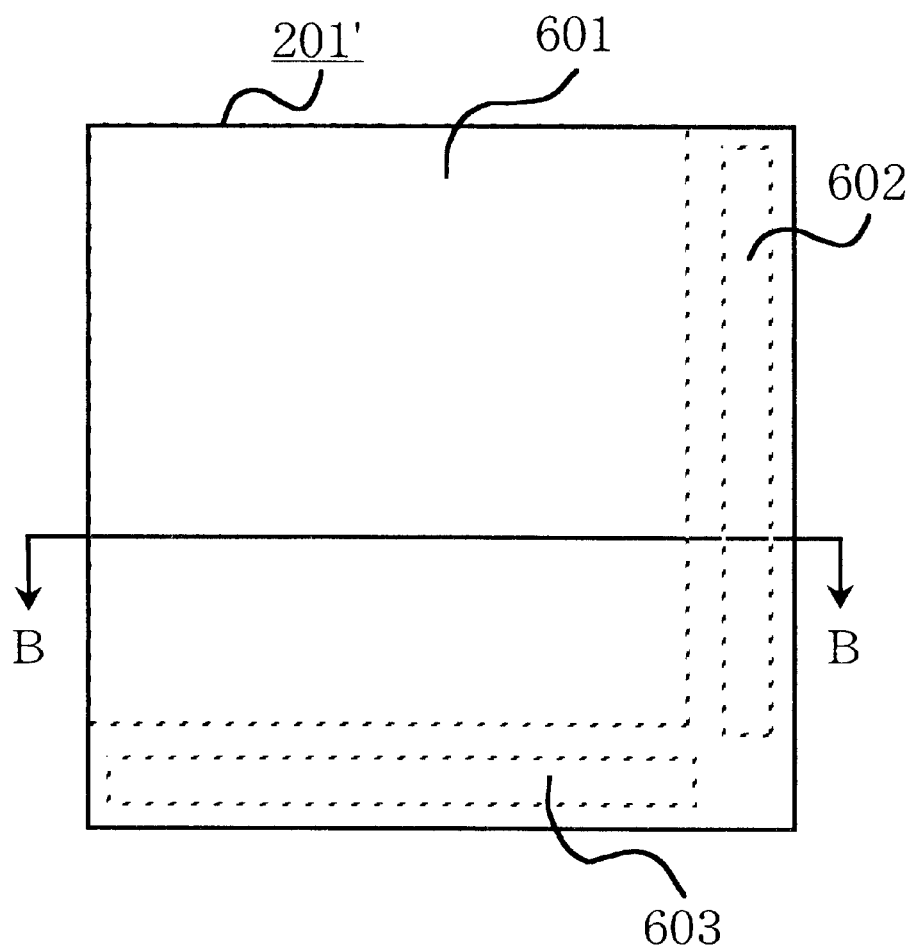
FIG. 18 is a plan view of another example of the arrangement of the X-ray detector unit.
Figure 19:
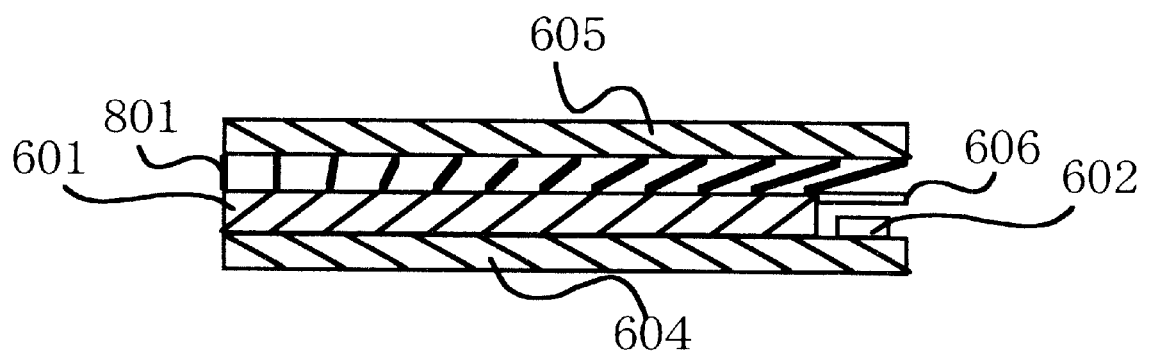
FIG. 19 is a cross-sectional view taken along B—B shown in FIG. 18.
Figure 20:
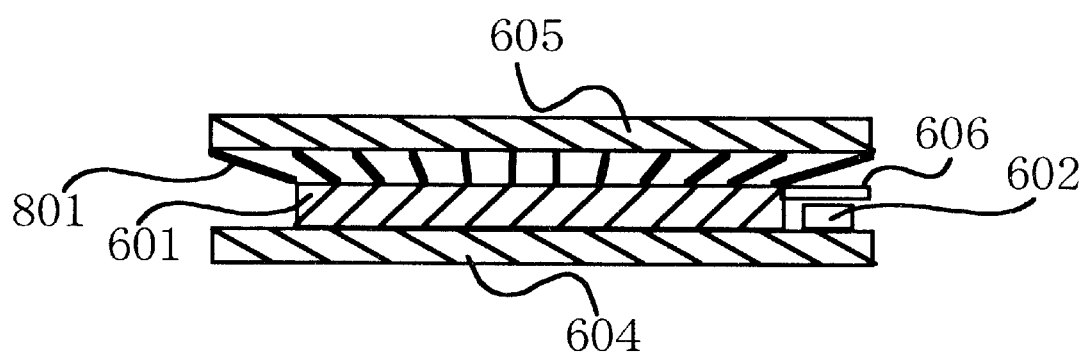
FIG. 20 is a cross-sectional view of an X-ray detector unit using a light-receiving element array having an area smaller than the area of the light-receiving element array shown in FIG. 19.

FIG. 18 is a plan view of another example of the arrangement of the X-ray detector unit, FIG. 19 is a cross-sectional view taken along B—B shown in FIG. 18, and FIG. 20 is a cross-sectional view of an x-ray detector unit using a light-receiving element array having an area smaller than the area of the light-receiving element array shown in FIG. 19. As shown in FIG. 19, in the X-ray detector unit 201', the light-receiving element array 601 is formed on the upper surface of the substrate 604, and the control circuit 602 is disposed at an end portion in the vicinity of a side of the substrate 604. A fiber plate 801 is disposed on top of the light-receiving element array 601, and the scintillator 605 of a size identical to that of the substrate 604 is disposed on top of the fiber plate 801. The X-ray shield 606 is disposed on top of the control circuit 602. The area of the fiber plate 801 on its side contacting the scintillator 605 is the same as the area of the scintillator. The fiber plate 801 and the light-receiving element array 601 are arranged such that the fibers in contact with the scintillator 605 contact the entire light-receiving element array 601. By virtue of the above-described construction, the light generated by the X-rays incident upon the region where the control circuit 602 is disposed can be guided to the light-receiving element array 601, and it is possible to detect the X-rays incident upon the scintillator 605 in the same way as the X-ray detector unit shown in FIG. 14. Accordingly, as shown in FIGS. 16 and 17, four or more X-ray detector units 201' can be arranged in an adjoining manner. In a case where the area of the light-receiving element array 601 is made smaller than the area of the scintillator 605 as shown in FIG. 20, it is possible to obtain advantages based on the arrangement shown in FIG. 19 by making the area of the fiber plate 801 on the side contacting the scintillator 605 identical to the area of the scintillator 605 and by making the area of the fiber plate 801 on the side contacting the light-receiving element array 601 identical to the area of the light-receiving element array 601.

<Description of an Outline of an Example of the Structure of the Light-Receiving Elements>

The light-receiving elements are each comprised of a photodiode portion, a common electrode connected to one end of the photodiode portion, a TFT switch portion having a source electrode to which the other end of the photodiode portion is connected, a gate line to which a gate electrode of the TFT switch portion is connected, and a signal line to which a drain electrode of the TFT switch portion is connected. The light-receiving elements are arranged in directions in which the gate line and the signal line extend, thereby forming the light-receiving element array. The size of the light-receiving element is, for example, 130 μm×130 m. The gate line and the signal line of each light-receiving element are connected to the gate and signal lines of an adjacently located light-receiving element, respectively, and are connected to the control circuit and the control reading circuit arranged at end portions of the light-receiving element array. The common electrode is also connected to the common electrode of an adjacently located light-receiving element. In the configuration of the first embodiment, the X-ray shields 606 are disposed so as to cover the gate electrode portions in order to prevent a malfunction of the TFT switch portions due to irradiation with X-rays.

First, a description will be given of the TFT switch portion. The photodiode portion for converting the visible light into an analog electrical signal, the TFT switch portion for switching an output of the electrical signal to the signal line, the gate line for controlling the switching of the TFT switch, and the like are formed on one surface (on the surface side upon which the visible light is incident) of a glass substrate by a known photolithographic technology. The gate electrode made of aluminum alloy is formed on the glass substrate, and a gate insulating film of silicon nitride is formed in such a manner as to cover the gate electrode. A channel layer of amorphous silicon is formed on the gate insulating film, and the drain electrode and the source electrode of aluminum alloy are formed on the channel layer. An insulating film of silicon nitride is formed on the drain electrode and the source electrode, and the X-ray shield 606 is further formed thereon.

In the photodiode portion, an insulating film formed integrally with the gate insulating film of silicon nitride is formed on the glass substrate, and the common electrode of aluminum alloy is formed on the insulating film. A photo-conductive film of amorphous silicon (a-Si:H) is formed on the common electrode, and a transparent electrode made of ITO is formed on an upper surface of the photoconductive film. The common electrode, the photoconductive film, and the transparent electrode are covered with the insulating film of silicon nitride. At an end portion of the photodiode portion, a connecting film is formed on the insulating film in such a manner as to extend to the region of the source electrode, and one end of the connecting film is connected to the transparent electrode through a contact hole provided in the insulating film, and the other end of the connecting film is connected to the source electrode. A fluorescent substance ma de of CsI and adapted to convert X-rays into visible light is disposed on the light-receiving surface side of the light-receiving element. It should be noted that the planar X-ray detector in accordance with the first embodiment can be constructed by one or more X-ray detector units.

Second Embodiment

Figure 21:
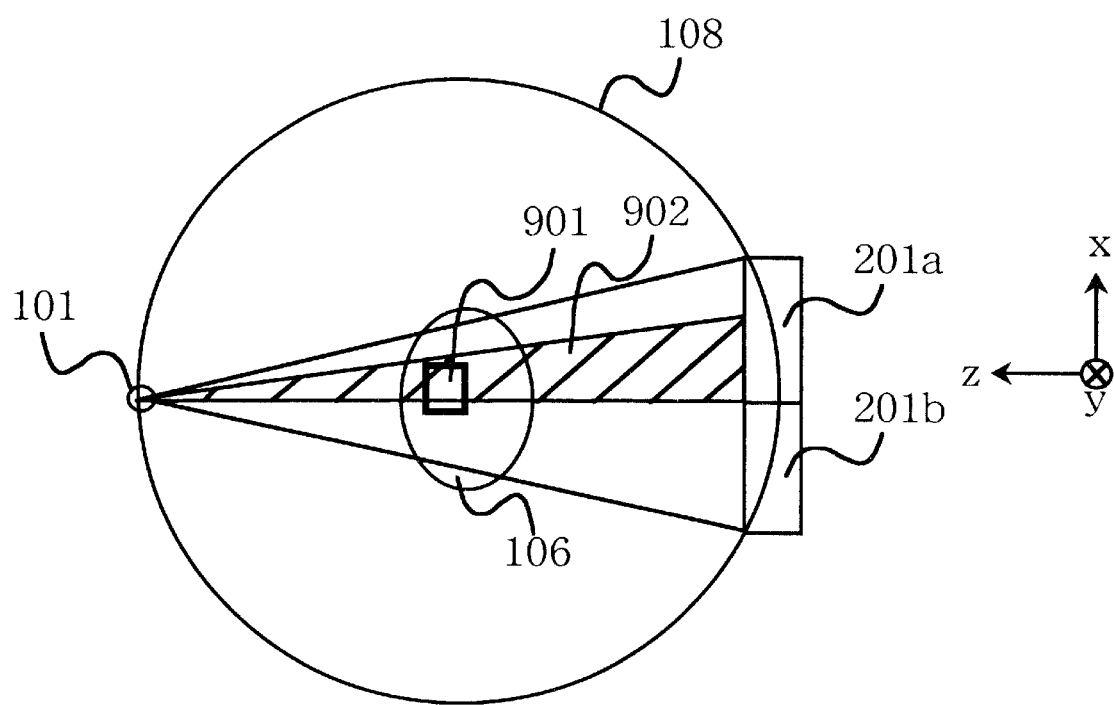
FIG. 21 is a diagram explaining a schematic configuration of an example of the X-ray based measuring device in accordance with a second embodiment of the invention, and is a diagram explaining the positional relationship between the imaging system and the interested area in a case where the interested area is set on a subject
Figure 22:
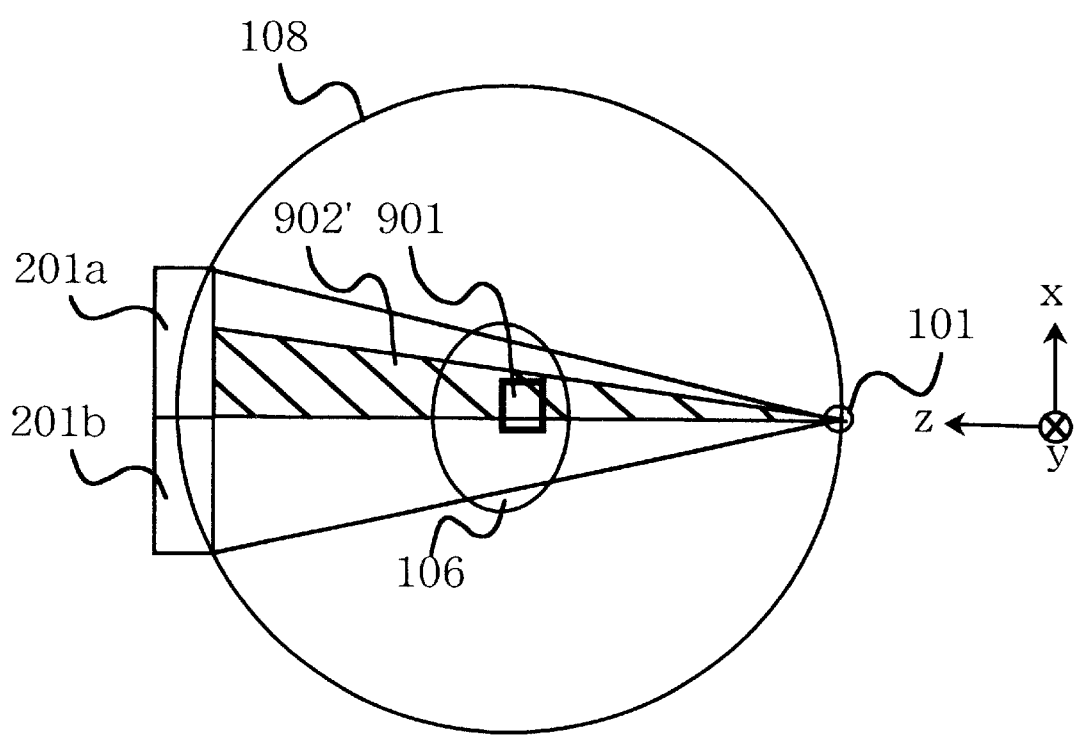
FIG. 22 is a diagram explaining the positional relationship between the imaging system and the interested area when the imaging system is rotated 180 degrees from the position shown in FIG. 21.
Figure 23:
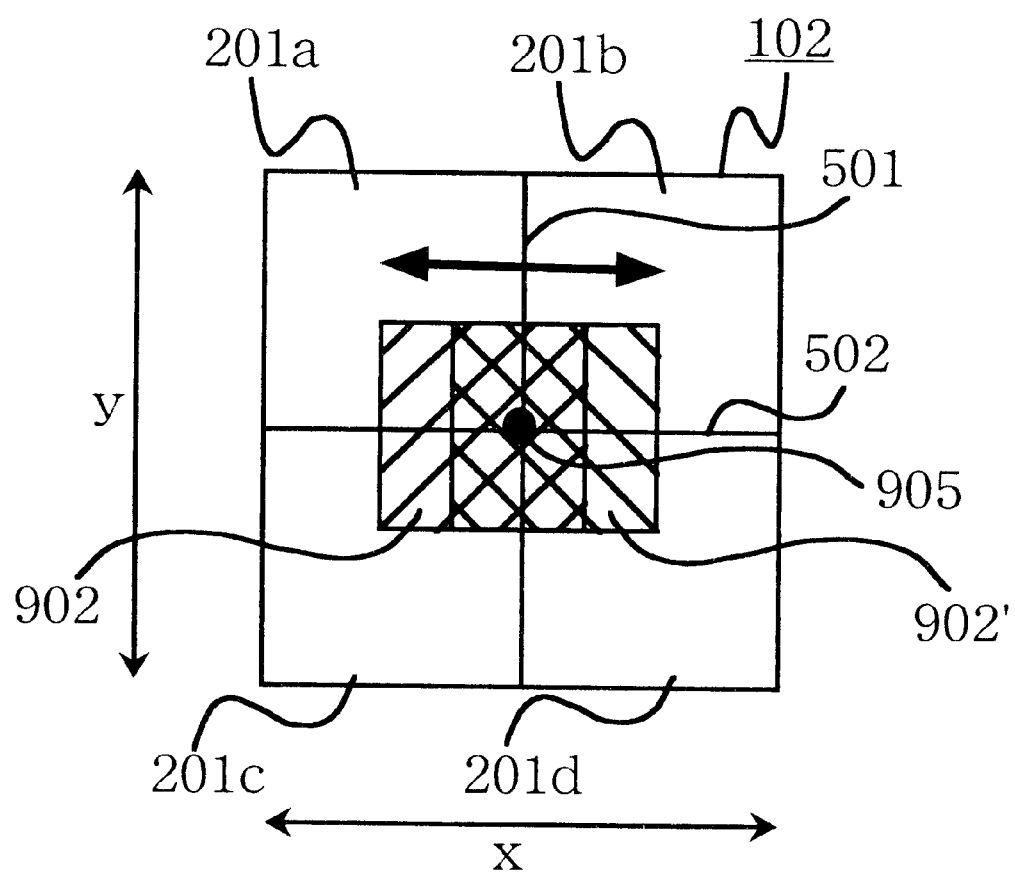
FIG. 23 is a diagram explaining the schematic configuration of the X-ray based measuring device in accordance with the second embodiment of the invention, and is a diagram explaining a change of the position of the interested area projected onto the planar X-ray detector consequent upon the rotation of the imaging system.

FIG. 21 is a diagram explaining a schematic configuration of an example of the X-ray based measuring device in accordance with a second embodiment of the invention, and is a diagram explaining the positional relationship between the imaging system and the interested area in a case where the interested area is set on the subject. FIG. 22 is a diagram explaining the positional relationship between the imaging system and the interested area when the imaging system is rotated 180 degrees from the position shown in FIG. 21. FIG. 23 is a diagram explaining the schematic configuration of the X-ray based measuring device in accordance with the second embodiment of the invention, and is a diagram explaining a change of the position of the interested area projected onto the planar X-ray detector consequent upon the rotation of the imaging system. The measuring device in accordance with the second embodiment is a cone beam X-ray CT device which is so arranged that the imaging system formed by the X-ray generator 101 and the planar X-ray detector 102 which are fixed is rotated around the subject 106, and in which a tomographic image of the subject 106 is reconstructed on the basis of a plurality of X-ray images obtained by picking up the images of the subject 106 from 360-degree directions around the subject 106.

The description of the measuring device of the second embodiment will be given only with respect to the procedure for setting the interested area in the planar X-ray detector whose arrangement differs from that of the measuring device of the first embodiment. In FIGS. 21, 22, and 23, reference numeral 901 indicates an interested area to be set on the subject, and numeral 902 denotes a projected area which is projected onto the light-receiving surface of the planar X-ray detector. The setting of the interested area 901 is effected by picking up an X-ray image of the subject, for instance, when the angle of rotation of the imaging system is 0 (zero), and on the basis of this X-ray image. The setting of the interested area 901 is not limited to the above-described method. For example, the chief DSP arithmetic portion 222 may determine the position of the interested area 901 through computation on the basis of the position of the interested area 901 in the interested area 901 in the X-ray image picked up in advance as well as the position of the imaging system.

When the angle of rotation of the imaging system is 0 (zero), as shown in FIG. 21, the interested area 901 set on the subject 106 is detected by the X-ray detector unit 1 (201a) and the X-ray detector unit 3 (201c) of the four X-ray detector units making up the planar X-ray detector 102. The projected area 902 of the interested area 901 for projection onto the light-receiving surfaces of the X-ray detector unit 1 (201a) and the X-ray detector unit 3 (201c) is at the position indicated by the slanting lines in FIG. 23. Next, when the picking up of the X-ray image is started, the projected area 902 of the interested area 901 for projection onto the light-receiving surface of the planar X-ray detector moves on the light-receiving surface of the planar X-ray detector in a direction (x direction) parallel to the rotational plane in conjunction with the rotation of the imaging system, and reaches a projected position 902' indicated by dotted lines in FIG. 23 when the angle of rotation of the imaging system is 180 degrees. At this time, the projected area on the light-receiving surface of the planar X-ray detector 102 moves up to the projected position 9021 indicated by dotted lines which are axially symmetrical with the projected position 902, which is indicated by the slanting lines, with respect to the connecting line 501 which represents the position where the X-ray detector unit 1 (201a) and the X-ray detector unit 2 (201b) contact with each other and the position where the X-ray detector unit 3 (201c) and the X-ray detector unit 4 (201d) contact with each other. Namely, as the imaging system is rotated, the position of the projected area of the interested area 901 for projection onto the light-receiving surface of the planar X-ray detector repeats the movement in the directions of arrows in the x directions shown in FIG. 23.

In the second embodiment, each unit DSP arithmetic portion 214 executes the picking up of X-ray images while moving the position of the interested area 901 set in the planar X-ray detector on the basis of the angle of rotation of the imaging system, and it is possible to attain advantages similar to those of the measuring device in accordance with the first embodiment. The picking up of X-ray images which is effected by setting the interested area 901 on the subject 106 is not limited to the cone beam CT device, and is also applicable to general X-ray measurement which is called radioscopy and radiography. In this case as well, imaging can be executed under optimum conditions with respect to the interested area 901 of the subject 106. Further, in IVR radioscopy which is represented by catheterization, it is possible to obtain an X-ray image in which a catheter can be always seen easily by fixing the interested area 901 on the specific object, i.e., the catheter. Accordingly, the examiner (operator) is able to easily operate the catheter, and the time required for catheterization can be shorted, so that it is possible to alleviate burdens imposed on the subject (patient) 106 and the examiner.

Third Embodiment

Figure 24:
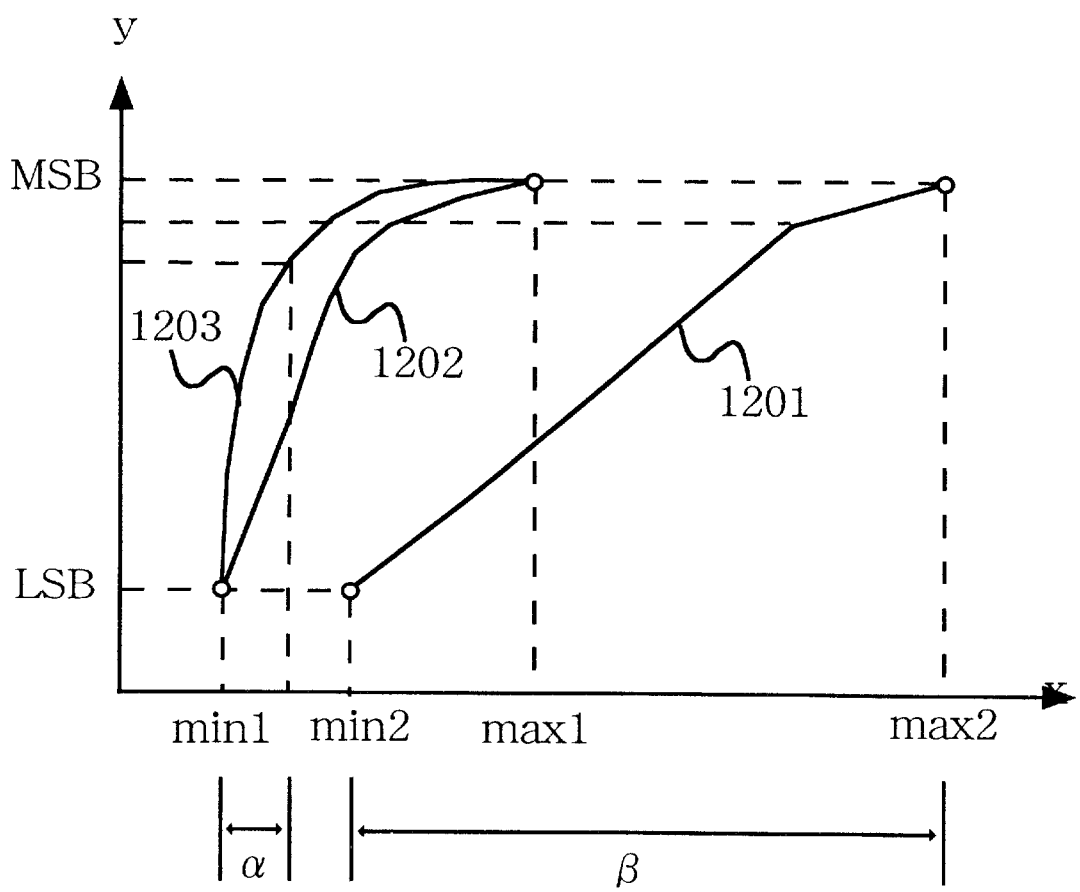
FIG. 24 is a diagram illustrating an example of the input output characteristics of input amplifiers of the measuring device in accordance with a third embodiment of the present invention.
Figure 25:
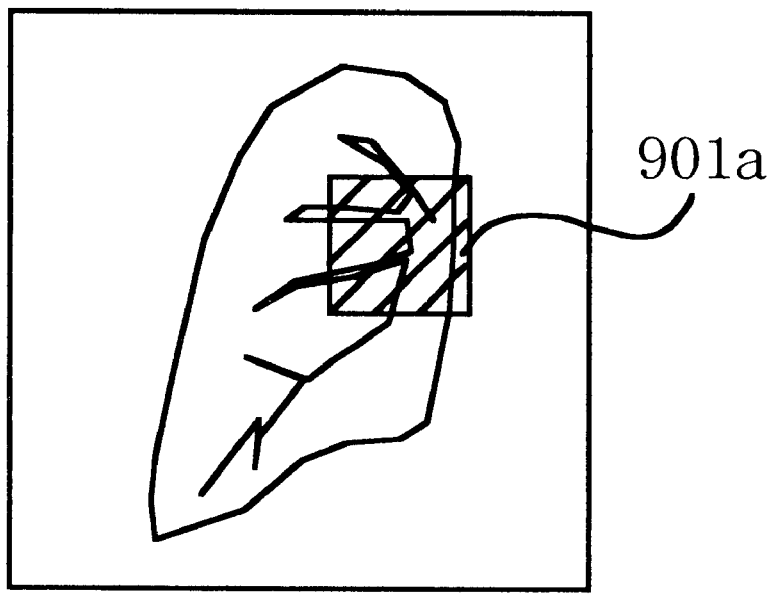
FIGS. 25, 26, 27, and 28 are diagrams explaining a schematic configuration of an example of a conventional X-ray based measuring device.
Figure 26:
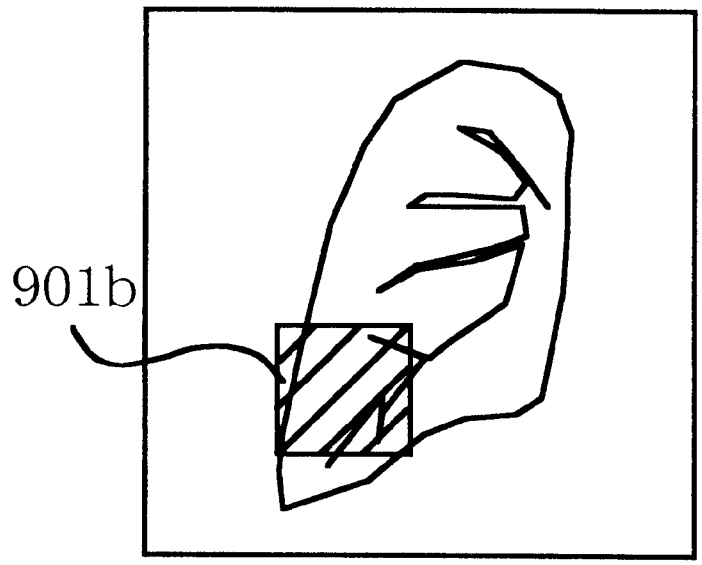
Figure 27:
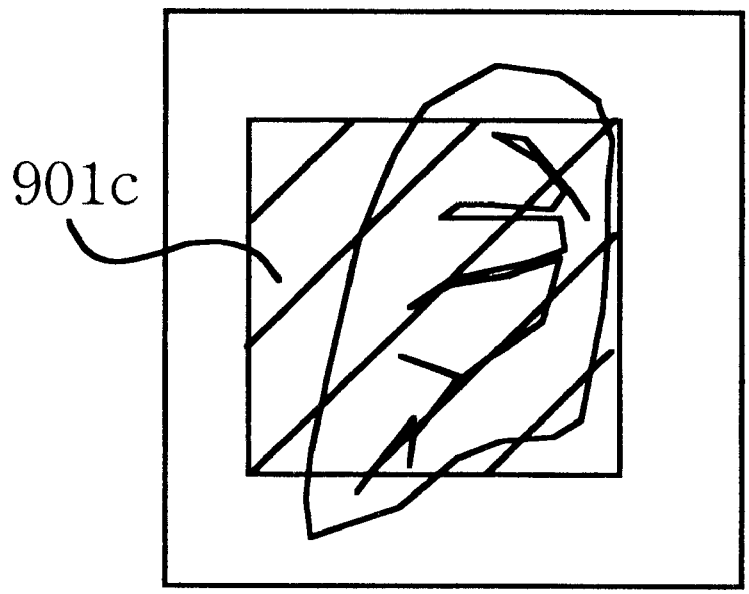
Figure 28:
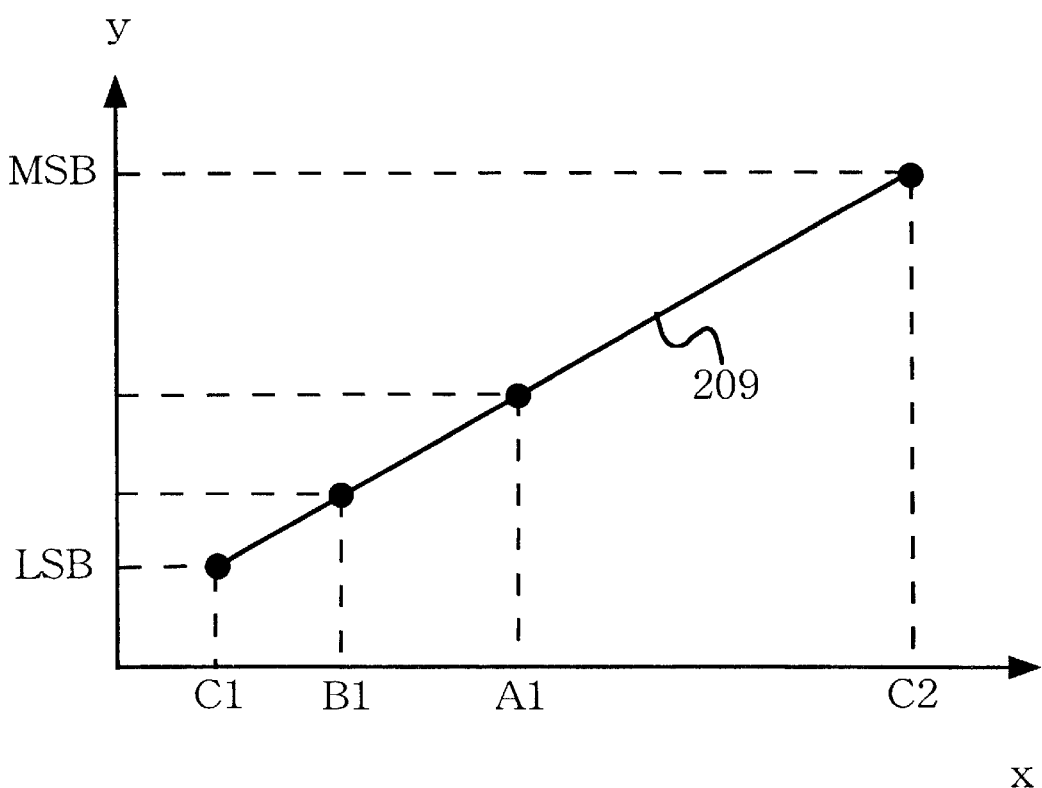

FIG. 24 is a diagram illustrating an example of the input output characteristics of the input amplifiers of the measuring device in accordance with a third embodiment of the present invention. In FIG. 24, the x-axis shows inputs to the input amplifier portions 211, while the y-axis shows outputs from the input amplifier portions 211. The other arrangements of the measuring device of the third embodiment excluding the input and output characteristics of the input amplifiers are identical to those of the first or second embodiment, and a description will be given hereafter of the input amplifiers alone. As shown in FIG. 24, in the measuring device of the third embodiment, the input output characteristic of the input amplifier portion 211 of the imaged-data collecting unit 1 is given by a nonlinear characteristic 1201, while the input output characteristic of the input amplifier portion 211 of the imaged-data collecting unit 2 is given by a nonlinear characteristic 1202. The nonlinear characteristic includes, for example, logarithmic conversion. In a case where the input amplifier portions 211 are logarithmic amplifiers, three parameters characterizing the input and output characteristics 1201 and 1202 include a logarithmic slope, an intercept (logarithmic offset), and an offset voltage, and the unit DSP arithmetic portions 214 are able to determine the three parameters and convert the input and output characteristics of the input amplifier portions 211, i.e., the conversion characteristics of the A/D converter portions 212, into nonlinear characteristics, as shown in FIG. 24.

If the conversion characteristics in the A/D converter portions 212 are made nonlinear characteristics, the examiner is able to effect A/D conversion by enlarging the dynamic range with respect to analog image signals corresponding to the neighborhood of predetermined pixel values on which particular attention is focused, so that the density resolution in the neighborhood of the predetermined pixel values can be improved in a case where the range of the analog image signals inputted to the input amplifier portions 211 are located in sections α and β. At this time, if the density resolution of digital image data obtained by the device (system) is set in advance by using as a reference the density resolution in the sections α and β where the density resolution during A/D conversion is high, and if the density resolution in the sections α and β is set in the neighborhood of the predetermined pixel values determined by a nonlinear characteristic 1203, it is possible to improve the density resolution in the neighborhood of the predetermined pixel values.

It should be noted that although, in the X-ray based measuring device described above, the arrangement provided is such that the X-ray detector units and the imaged-data collecting units are provided one-to-one, the invention is not limited to this arrangement, and advantages similar to those described earlier can be offered also in a case where the planar X-ray detector 102 is formed by a single X-ray detector unit, and the imaged-data collecting units fetch analog image signals by assuming that the planar X-ray detector 102 is formed by a plurality of X-ray detector units during the reading of the analog image signals.

Although a detailed description has been given of the present invention on the basis of the embodiments, the present invention is not limited to the above-described embodiments, and various modifications are possible within a range which does not depart from its gist. Typical advantages of the present invention can be described briefly as follows. (1) The dynamic range of the measuring device using the planar X-ray detector can be enlarged. (2) High-speed imaging is possible by using a planar X-ray detector. (3) The dynamic range of the planar X-ray detector can be effectively utilized. (4) It is possible to improve the quality of X-ray images measured by using the planar X-ray detector.

What is claimed is:

1. An X-ray based measuring device comprising:

X-ray imaging means which has a detection area divided into a plurality of X-ray detector units, detects X-rays transmitted through an inspection object, and picks up an X-ray image in an interested area of the inspection object;

first conversion means for converting analog image signals read from the X-ray detector units into digital image data under specified first conversion conditions for each of the X-ray detector units; and second conversion means for converting the digital image data obtained for each of the X-ray detector units under second conversion conditions corresponding to the specified first conversion conditions.

2. An X-ray based measuring device according to claim 1, further comprising setting means for setting the specified first conversion conditions for each of the X-ray detector units based on the analog image signals in the interested area set in advance.

3. An X-ray based measuring device according to claim 1, wherein the first conversion means includes an A/D converter; and wherein a range of an input signal to the A/D converter and a range of a signal detected by the X-ray detector units are made to agree with each other.

4. An X-ray based measuring device according to claim 1, wherein the first conversion means includes an A/D converter and linear amplification means for linearly amplifying the signal detected by the X-ray detector units and/or nonlinear amplification means for nonlinearly amplifying the same, so as to change an operating condition of the A/D converter by one of first parameters including a gain and an offset of the linear amplification means and second parameters including a gain and a nonlinearity of an input output characteristic of the nonlinear amplification means, or by a combination of the first and second parameters.

5. An X-ray based measuring device according to claim 4, wherein the nonlinear amplification means is constituted by logarithmic amplification means; and wherein the gain and the nonlinearity of the input output characteristic of the nonlinear amplification means are set by a logarithmic slope, an intercept voltage, and an offset voltage of the logarithmic amplification means.

6. An X-ray based measuring device according to claim 1, wherein the second conversion means determines a maximum value and a minimum value in the interested area set in advance for each of the X-ray detector units, and determines X-ray conditions in ensuing imaging based on the maximum value and the minimum value.

7. An X-ray based measuring device according to claim 1, further comprising:

rotating means for rotating about the inspection object X-ray irradiating means for irradiating the inspection object with X-rays and the X-ray imaging means; and reconstructing means for reconstructing an X-ray tomographic image or a three-dimensional reconstructed image of the inspection object based on a plurality of X-ray images picked up.

8. An X-ray based measuring device according to claim 7, wherein the rotating means is a means for helically rotating and moving the X-ray irradiating means and the X-ray imaging means about the inspection object.

9. An X-ray based measuring device according to claim 1, further comprising means for changing the interested area set in advance for each direction in which an image of the inspection object is picked up.

10. An X-ray based measuring device comprising:

X-ray imaging means which has a detection area divided into a plurality of X-ray detector units, detects X-rays transmitted through an inspection object, and picks up an X-ray image in an interested area of the inspection object;

first conversion means for converting analog image signals read sequentially from the X-ray detector units starting with detecting elements of the X-ray detector units which are closest to a line representing a position where two of the X-ray detector units contact each other into digital image data under specified first conversion conditions for each of the X-ray detector units; and second conversion means for converting the digital image data obtained for each of the X-ray detector units under second conversion conditions corresponding to the specified first conversion conditions.

11. An X-ray based measuring device according to claim 10, further comprising setting means for setting the specified first conversion conditions for each of the X-ray detector units based on the analog image signals in the interested area set in advance.

12. An X-ray based measuring device according to claim 10, wherein the first conversion means includes an A/D converter; and wherein a range of an input signal to the A/D converter and a range of a signal detected by the X-ray detector units are made to agree with each other.

13. An X-ray based measuring device according to claim 10, wherein the first conversion means includes an A/D converter and linear amplification means for linearly amplifying the signal detected by the X-ray detector units and/or nonlinear amplification means for nonlinearly amplifying the same, so as to change an operating condition of the A/D converter by one of first parameters including a gain and an offset of the linear amplification means and second parameters including a gain and a nonlinearity of an input output characteristic of the nonlinear amplification means, or by a combination of the first and second parameters.

14. An X-ray based measuring device according to claim 13, wherein the nonlinear amplification means is constituted by logarithmic amplification means; and wherein the gain and the nonlinearity of the input output characteristic of the nonlinear amplification means are set by a logarithmic slope, an intercept voltage, and an offset voltage of the logarithmic amplification means.

15. An X-ray based measuring device according to claim 10, wherein the second conversion means determines a maximum value and a minimum value in the interested area set in advance for each of the X-ray detector units, and determines X-ray conditions in ensuing imaging based on the maximum value and the minimum value.

16. An X-ray based measuring device according to claim 10, further comprising:
   rotating means for rotating about the inspection object X-ray irradiating means for irradiating the inspection object with X-rays and the X-ray imaging means; and
   reconstructing means for reconstructing an X-ray tomographic image or a three-dimensional reconstructed image of the inspection object based on a plurality of X-ray images picked up.

17. An X-ray based measuring device according to claim 16, wherein the rotating means is a means for helically rotating and moving the X-ray irradiating means and the X-ray imaging means about the inspection object.

18. An X-ray based measuring device according to claim 10, further comprising means for changing the interested area set in advance for each direction in which an image of the inspection object is picked up.

19. An X-ray based measuring device comprising:
   X-ray imaging means which has a detection area divided into a plurality of X-ray detector units, detects X-rays transmitted through an inspection object, and picks up an X-ray image of the inspection object; and
   reading means for reading analog image signals sequentially from the X-ray detector units starting with detecting elements of the X-ray detector units which are closest to a position representing a line where two of the X-ray detector units contact each other.

20. An X-ray based measuring device comprising:
   X-ray imaging means which includes an X-ray detector formed by arranging in an adjoining manner a plurality of X-ray detector units, each of the X-ray detector units including a plurality of detecting elements, the X-ray imaging means being adapted to detect X-rays transmitted through an inspection object so as to pick up an X-ray image in an interested area of the inspection object set in advance;
   first conversion means provided in correspondence with the X-ray detector units and adapted to convert analog image signals read independently by each of the X-ray detector units into digital image data under specified conversion conditions for each of the X-ray detector units; and
   second conversion means for converting the digital image data obtained for each of the X-ray detector units so as to convert a relationship of correspondence between the analog image signals and the digital image data which is different for each of the X-ray detector units and is based on the specified conversion conditions for each of the X-ray detector units into a relationship of correspondence between the analog image signals and the digital image data which is set in advance for each of the X-ray detector units.

21. An X-ray based measuring device according to claim 20, further comprising setting means for setting the specified conversion conditions for each of the X-ray detector units based on the analog image signals in the interested area detected by each of the X-ray detector units.

22. An X-ray based measuring device according to claim 20, wherein the first conversion means includes an A/D converter; and
   wherein a range of a magnitude of an input signal to the A/D converter and a range of a magnitude of a signal detected by the X-ray detector units are made to agree with each other.

23. An X-ray based measuring device according to claim 20, wherein the first conversion means includes an A/D converter and linear amplification means for linearly amplifying the signal detected by the X-ray detector units and/or nonlinear amplification means for nonlinearly amplifying the same, so as to change an operating condition of the A/D converter by one of first parameters including a gain and an offset of the linear amplification means and second parameters including a gain and a nonlinearity of an input output characteristic of the nonlinear amplification means, or by a combination of the first and second parameters.

24. An X-ray based measuring device according to claim 23, wherein the nonlinear amplification means is constituted by logarithmic amplification means; and
   wherein the gain and the nonlinearity of the input output characteristic of the nonlinear amplification means are set by a logarithmic slope, an intercept voltage, and an offset voltage of the logarithmic amplification means.

25. An X-ray based measuring device according to claim 20, wherein the second conversion means determines X-ray conditions in ensuing imaging based on a maximum value and a minimum value in the interested area detected by each of the X-ray detector units.

26. An X-ray based measuring device according to claim 20, further comprising means for changing the interested area for each direction in which an image of the inspection object is picked up.

27. An X-ray based measuring device comprising:
   X-ray imaging means which includes an X-ray detector, the X-ray detector being formed by arranging in an adjoining manner a plurality of X-ray detector units, each of the X-ray detector units including a plurality of detecting elements, the X-ray imaging means being adapted to detect X-rays transmitted through an inspection object so as to pick up an X-ray image in an interested area of the inspection object set in advance; and
   conversion means provided in correspondence with the X-ray detector units and adapted to convert analog image signals read independently by each of the X-ray detector units into digital image data under specified conversion conditions for each of the X-ray detector units;
   wherein the analog image signals of the detecting elements corresponding to pixels in the interested area are sequentially read respectively independently by the conversion means respectively corresponding to two of the X-ray detector units, starting with the detecting elements corresponding to the pixels in the interested area which are closest to a line representing a position where the two of the X-ray detector units contact each other in a center of a visual field of the X-ray detector.

28. An X-ray based measuring device comprising:
   X-ray imaging means which includes an X-ray detector, the X-ray detector being formed by arranging in an adjoining manner a plurality of X-ray detector units, each of the X-ray detector units including a plurality of detecting elements, the X-ray imaging means being adapted to detect X-rays transmitted through an inspection object so as to pick up an X-ray image in an interested area of the inspection object set in advance; and
   conversion means provided in correspondence with the X-ray detector units and adapted to convert analog image signals read independently by each of the X-ray detector units into digital image data under specified conversion conditions for each of the X-ray detector units;

wherein the analog image signals are sequentially read starting with the detecting elements corresponding to pixels in the interested area which are closest to a central position of a visual field of the X-ray detector.

29. An X-ray based measuring device comprising:

X-ray imaging means which include an X-ray detector, the X-ray detector including a plurality of detecting elements, the X-ray imaging means being adapted to detect X-rays transmitted through an inspection object so as to pick up an X-ray image in an interested area of the inspection object set in advance by assuming that the X-ray detector is formed by a plurality of X-ray detector units collectively including the plurality of detecting elements;

first conversion means provided in correspondence with the X-ray detector units and adapted to convert analog image signals read independently by each of the X-ray detector units into digital image data under specified conversion conditions for each of the X-ray detector units; and second conversion means for converting the digital image data obtained for each of the X-ray detector units so as to convert a relationship of correspondence between the analog image signals and the digital image data which is different for each of the X-ray detector units and is based on the specified conversion conditions for each of the X-ray detector units into a relationship of correspondence between the analog image signals and the digital image data which is set in advance for each of the X-ray detector units.

30. An X-ray based measuring device according to claim 29, further comprising setting means for setting the specified conversion conditions for each of the X-ray detector units based on the analog image signals in the interested area.

31. An X-ray based measuring device according to claim 29, wherein the first conversion means includes an A/D converter; and wherein a range of a magnitude of an input signal to the A/D converter and a range of a magnitude of a signal detected by the X-ray detector units are made to agree with each other.

32. An X-ray based measuring device according to claim 29, wherein the second conversion means determines a maximum value and a minimum value in the interested area for each of the X-ray detector units, and determines X-ray conditions in ensuing imaging based on the maximum value and the minimum value.

33. An X-ray based measuring device according to claim 29, further comprising means for changing the interested area for each direction in which an image of the inspection object is picked up.

34. An X-ray based measuring device comprising:

X-ray imaging means which includes an X-ray detector, the X-ray detector including a plurality of detecting elements, the X-ray imaging means being adapted to detect X-rays transmitted through an inspection object so as to pick up an X-ray image in an interested area of the inspection object set in advance by assuming that the X-ray detector is formed by a plurality of X-ray detector units collectively including the plurality of detecting elements; and conversion means provided in correspondence with the X-ray detector units and adapted to convert analog image signals read independently by each of the X-ray detector units into digital image data under specified conversion conditions for each of the X-ray detector units;

wherein the analog image signals of the detecting elements corresponding to pixels in the interested area are sequentially read respectively independently by the conversion means respectively corresponding to two of the X-ray detector units, starting with the detecting elements corresponding to the pixels in the interested area which are closest to a line representing a position where the two of the X-ray detector units contact each other in a neighborhood of a center of a visual field of the X-ray detector.

35. An X-ray based measuring device comprising:

X-ray imaging means which include an X-ray detector, the X-ray detector including a plurality of detecting elements, the X-ray imaging means being adapted to detect X-rays transmitted through an inspection object so as to pick up an X-ray image in an interested area of the inspection object set in advance by assuming that the X-ray detector is formed by a plurality of X-ray detector units collectively including the plurality of detecting elements; and conversion means provided in correspondence with the X-ray detector units and adapted to convert analog image signals read independently by each of the X-ray detector units into digital image data under specified conversion conditions for each of the X-ray detector units;

wherein the analog image signals are sequentially read starting with the detecting elements corresponding to pixels in the interested area which are closest to a central position of a visual field of the X-ray detector.

* * * * *